US007008623B1

(12) United States Patent
Bonnefoy et al.

(10) Patent No.: US 7,008,623 B1
(45) Date of Patent: Mar. 7, 2006

(54) ANTIBODIES TO CD23, DERIVATIVES THEREOF, AND THEIR THERAPEUTIC USES

(75) Inventors: Jean-Yves Marcel Paul Bonnefoy, Le Sappey (FR); James Scott Crowe, Stevenage (GB); Jonathan Henry Ellis, Ware (GB); Nicholas Timothy Rapson, Cambridge (GB); Jean Shearin, Durham, NC (US)

(73) Assignee: Glaxo Wellcome Inc., Research Triangle Park, NC (US)

( * ) Notice: Subject to any disclaimer, the term of this patent is extended or adjusted under 35 U.S.C. 154(b) by 0 days.

(21) Appl. No.: 09/674,716

(22) PCT Filed: May 7, 1999

(86) PCT No.: PCT/GB99/01434

§ 371 (c)(1),
(2), (4) Date: Jan. 22, 2001

(87) PCT Pub. No.: WO99/58679

PCT Pub. Date: Nov. 18, 1999

(30) Foreign Application Priority Data

May 9, 1998 (GB) ..................................... 9809839

(51) Int. Cl.
*C12P 21/08* (2006.01)
*C07K 16/28* (2006.01)
*A61K 39/395* (2006.01)

(52) U.S. Cl. .............................. 424/143.1; 530/387.3; 530/388.1; 530/388.22

(58) Field of Classification Search ............. 530/387.3, 530/388.22, 388.1; 424/143.1, 133
See application file for complete search history.

(56) References Cited

U.S. PATENT DOCUMENTS 5,658,570 A * 8/1997 Newman et al.
6,011,138 A * 1/2000 Reff et al.

FOREIGN PATENT DOCUMENTS

GB 0788513 B 1 * 2/1996
WO 93/02108 2/1993
WO 96/12741 5/1996
WO 98/37099 8/1998

OTHER PUBLICATIONS

Abaza et al, J of Protein Chemistry 11(5): 433-444, 1992.*
Ngo et al., 1994, The Protein Folding Problem and Tertiary Structure Prediction, pp. 492-495.*
Kuby et al., 1994, Immunology, second edition, pp. 85-96.*
Couzin et al, Science 300: 1862-1865, Jun. 2003.*
Van Noort et al, International Review of Cytology 178: 127-206, 1998.*
Bodey et al, Anticancer Research 20: 2665-2676, 2000.*
Spitler et al, Cancer Biotherapy 10: 1-3, 1995.*
Ward et al, Therapeutic Immunology 2: 77-94, 1995.*
Mavromatis et al, J Clin Oncology 21(9): 1874-1881, 2003.*
Wakai et al, Hybridoma 12(1): 25-43, Feb. 1993.*
J. Bonnefoy et al.: "Production and characterization of a monoclonal antibody specific for the human lymphocyte low affinity receptor for IgE: CD23 is a low affinity receptor for IgE." The Journal of Immunology, vol. 138, No. 9, (May 1987) pp. 2970-2978, Baltimore, MD, USA.
C. Plater-Zyberk et al.: "Marked amelioration of established collagen-induced arthritis by treatment with antibodies to CD23 in vivo." Nature Medicine, vol. 1, No. 8, (Aug. 1995) pp. 781-785, New York, NY, USA.
L. Flores-Romo et al.: "Inhibition of an in vivo antigen-specific IgE response by antibodies to CD23." Science, vol. 261, No. 5124, (Aug. 1993) pp. 1038-1041, Washington, DC, USA.
Kleinau et al. "Importance of CD23 for collagen-induced arthritis: Delayed onset and reduced severity in CD23-deficient mice" J. Immunol. 162:4266-4270 (1999).

* cited by examiner

*Primary Examiner*—Christina Chan
*Assistant Examiner*—Phuong Huynh
(74) *Attorney, Agent, or Firm*—Elizabeth J. Hecht

(57) ABSTRACT

The invention relates to antibodies which bind to the CD23 (FCεRII) type II molecule particularly altered antibodies including antibodies which bind to the CD23 (FCεRII) type II molecule characterized by an affinity constant equal to or greater than $1 \times 10^9$ Ka Mol$^{-1}$, the preparation of such antibodies, pharmaceutical compositions which contain such antibodies and their use in therapy particularly in the treatment of autoimmune and inflammatory disorders.

10 Claims, 6 Drawing Sheets

```
      AAGCTTTACAGTTACTCAGCACACAGGACCTCACCATGGATTTTGGGCTGATTTTTTTA
    1 ------------------------------------------------------------ 60
      TTCGAAATGTCAATGAGTCGTGTGTCCTGGAGTGGTACCTAAAACCCGACTAAAAAAAT
C       A  L  Q  L  L  S  T  Q  D  L  T  M  D  F  G  L  I  F  F  I  -

TTGTTCTTTTAAAAGGGGTCCAGAGTGAAGTGAAGCTTGAGGAGTCTGGAGGAGGCTTGG
   61 ------------------------------------------------------------ 120
      AACAAGAAAATTTTCCCCAGGTCTCACTTCACTTCGAACTCCTCAGACCTCCTCCGAACC
C       V  L  L  K  G  V  Q  S  E  V  K  L  E  E  S  G  G  G  L  V  -

TGCAACCTGGAGGATCCATGAAACTCTCCTGTGTAGCCTCTGGATTTACTTTCAGTGGCT
  121 ------------------------------------------------------------ 180
      ACGTTGGACCTCCTAGGTACTTTGAGAGGACACATCGGAGACCTAAATGAAAGTCACCGA
C       Q  P  G  G  S  M  K  L  S  C  V  A  S  G  F  T  F  S  G  Y  -

ACTGGATGTCTTGGGTCCGCCAGTCTCCAGAGAAGGGGCTTGAGTGGGTTGCTGAAATTA
  181 ------------------------------------------------------------ 240
      TGACCTACAGAACCCAGGCGGTCAGAGGTCTCTTCCCCGAACTCACCCAACGACTTTAAT
C       W  M  S  W  V  R  Q  S  P  E  K  G  L  E  W  V  A  E  I  R  -

GATTGAAATCTGATAATTATGCAACACATTATGCGGAGTCTGTGAAAGGGAAGTTCACCA
  241 ------------------------------------------------------------ 300
      CTAACTTTAGACTATTAATACGTTGTGTAATACGCCTCAGACACTTTCCCTTCAAGTGGT
C       L  K  S  D  N  Y  A  T  H  Y  A  E  S  V  K  G  K  F  T  I  -

TCTCAAGAGATGATTCCAAAAGTCGTCTCTACCTGCAAATGAACAGCTTAAGAGCTGAAG
  301 ------------------------------------------------------------ 360
      AGAGTTCTCTACTAAGGTTTTCAGCAGAGATGGACGTTTACTTGTCGAATTCTCGACTTC
C       S  R  D  D  S  K  S  R  L  Y  L  Q  M  N  S  L  R  A  E  D  -

ACAGTGGAGTTTATTACTGTACAGATTTCATAGACTGGGGCCAAGGGACACTAGT
  361 ------------------------------------------------------ 415
      TGTCACCTCAAATAATGACATGTCTAAAGTATCTGACCCCGGTTCCCTGTGATCA
C       S  G  V  Y  Y  C  T  D  F  I  D  W  G  Q  G  T  L
```

FIG. 1

```
        AAGCTTTACAGTTACTCAGCACACAGGACCTCACCATGAGGTTCTCTGTTCAGTTTCTGG
      1 ---------+---------+---------+---------+---------+---------+ 60
        TTCGAAATGTCAATGAGTCGTGTGTCCTGGAGTGGTACTCCAAGAGACAAGTCAAAGACC

C          A   L   Q   L   L   S   T   Q   D   L   T   M   R   F   S   V   Q   F   L   G   -

GGGTGCTTATGTTCTGGATCTCTGGAGTCAGTGGGGATATTGTGATAACCCAGGATGAAC
     61 ---------+---------+---------+---------+---------+---------+ 120
        CCCACGAATACAAGACCTAGAGACCTCAGTCACCCCTATAACACTATTGGGTCCTACTTG

C          V   L   M   F   W   I   S   G   V   S   G   D   I   V   I   T   Q   D   E   L   -

TCTCCAATCCTGTCACTTCTGGAGAATCAGTTTCCATCTCCTGCAGGTCTAGTAAGAGTC
    121 ---------+---------+---------+---------+---------+---------+ 180
        AGAGGTTAGGACAGTGAAGACCTCTTAGTCAAAGGTAGAGGACGTCCAGATCATTCTCAG

C          S   N   P   V   T   S   G   E   S   V   S   I   S   C   R   S   S   K   S   L   -

TCCTGTATAAGGATGGGAAGACATACTTGAATTGGTTTCTGCAGAGACCAGGACAATCTC
    181 ---------+---------+---------+---------+---------+---------+ 240
        AGGACATATTCCTACCCTTCTGTATGAACTTAACCAAAGACGTCTCTGGTCCTGTTAGAG

C          L   Y   K   D   G   K   T   Y   L   N   W   F   L   Q   R   P   G   Q   S   P   -

CTCAGCTCCTGATGTATTTGATGTCCACCCGTGCATCAGGAGTCTCAGACCGGTTTAGTG
    241 ---------+---------+---------+---------+---------+---------+ 300
        GAGTCGAGGACTACATAAACTACAGGTGGGCACGTAGTCCTCAGAGTCTGGCCAAATCAC

C          Q   L   L   M   Y   L   M   S   T   R   A   S   G   V   S   D   R   F   S   G   -

GCAGTGGGTCAGGCACAGATTTCACCCTGGAAATCAGTAGAGTGAAGGCTGAGGATGTGG
    301 ---------+---------+---------+---------+---------+---------+ 360
        CGTCACCCAGTCCGTGTCTAAAGTGGGACCTTTAGTCATCTCACTTCCGACTCCTACACC

C          S   G   S   G   T   D   F   T   L   E   I   S   R   V   K   A   E   D   V   G   -

GTGTGTATTACTGTCAACAACTTGTAGAGTATCCATTCACGTTCGGCTCGGGGACAAAGT
    361 ---------+---------+---------+---------+---------+---------+ 420
        CACACATAATGACAGTTGTTGAACATCTCATAGGTAAGTGCAAGCCGAGCCCCTGTTTCA

C          V   Y   Y   C   Q   Q   L   V   E   Y   P   F   T   F   G   S   G   T   K   L   -

TGGAAATAAAACGTACG
    421 ----------------- 437
        ACCTTTATTTTGCATGC

```
        GATATTGTGATGACTCAGTCTCCACTCTCCCTGCCCGTCACCCCTGGAGAGCCGGCCTCC
    1   ---------+---------+---------+---------+---------+---------+ 60
        CTATAACACTACTGAGTCAGAGGTGAGAGGGACGGGCAGTGGGGACCTCTCGGCCGGAGG
             FRI
A       [D   I   V   M   T   Q   S   P   L   S   L   P   V   T   P   G   E   P   A   S  -
                 69 70                                                          117 118
        ATCTCCTGTCGCTCGAGTAAGAGTCTCCTGTATAAGGATGGGAAGACATACTTGAATTGG
   61   ---------+---------+---------+---------+---------+---------+ 120
        TAGAGGACAGCGAGCTCATTCTCAGAGGACATATTCCTACCCTTCTGTATGAACTTAACC
                                             CDR1
A       I   S   C] [R   S   S   K   S   L   L   Y   K   D   G   K   T   Y   L   N] [W  -
                                                                162 163
        TACCTGCAGAAGCCAGGGCAGTCTCCACAGCTCCTGATCTATTTGATGTCCACCCGGGCA
  121   ---------+---------+---------+---------+---------+---------+ 180
        ATGGACGTCTTCGGTCCCGTCAGAGGTGTCGAGGACTAGATAAACTACAGGTGGGCCCGT
                      FR2                                     CDR2
A       Y   L   Q   K   P   G   Q   S   P   Q   L   L   I   Y] [L   M   S   T   R   A  -
        183 184
        TCAGGGGTCCCTGACAGGTTCAGTGGCAGTGGATCAGGCACAGATTTTACACTGAAAATC
  181   ---------+---------+---------+---------+---------+---------+ 240
        AGTCCCCAGGGACTGTCCAAGTCACCGTCACCTAGTCCGTGTCTAAAATGTGACTTTTAG
                                              FR3
A       S] [G   V   P   D   R   F   S   G   S   G   S   G   T   D   F   T   L   K   I  -
                                                        279 280
        AGCAGAGTGGAGGCTGAGGATGTTGGGGTTTATTACTGTCAACAGCTGGTAGAGTATCCA
  241   ---------+---------+---------+---------+---------+---------+ 300
        TCGTCTCACCTCCGACTCCTACAACCCCAAATAATGACAGTTGTCGACCATCTCATAGGT
                                                             CDR3
A       S   R   V   E   A   E   D   V   G   V   Y   Y   C] [Q   Q   L   V   E   Y   P  -
            306 307                                      339 340
        TTCACGTTCGGCCAAGGGACCAAGGTGGAGATCAAACGTACGGTGGCT
  301   ---------+---------+---------+---------+-------- 348
        AAGTGCAAGCCGGTTCCCTGGTTCCACCTCTAGTTTGCATGCCACCGA
                               FR4
A       F   T] [F   G   Q   G   T   K   V   E   I   K   R]  T   V   A   -
```

```
     GAGGTGCAGCTGGTGGAGTCTGGGGGAGGCTTGGTAAAGCCCGGGGGGTCCCTTAGACTC
  1  ------------+---------+---------+---------+---------+---------+ 60
     CTCCACGTCGACCACCTCAGACCCCCTCCGAACCATTTCGGGCCCCCCAGGGAATCTGAG
                                      FR1
A    [E  V  Q  L  V  E  S  G  G  G   L  V  K  P  G  G  S  L  R  L    -
                                  90  91              105  106
     TCCTGTGCAGCTAGCGGATTCACTTTCAGTGGCTACTGGATGTCCTGGGTCCGCCAGGCT
 61  ------------+---------+--------+---------+----+----+---------+ 120
     AGGACACGTCGATCGCCTAAGTGAAAGTCACCGATGACCTACAGGACCCAGGCGGTCCGA
                                                       CDR1
A    S  C  A  A  S  G  F  T  F  S] [G  Y  W  M  S] [W  V  R  Q  A    -
                                147  148
     CCAGGGAAGGGGCTCGAGTGGGTTGCTGAAATTAGATTGAAATCTGATAATTATGCAACA
121  ------------+---------+------+--+---------+---------+---------+ 180
     GGTCCCTTCCCCGAGCTCACCCAACGACTTTAATCTAACTTTAGACTATTAATACGTTGT
                    FR2                                    CDR2
A    P  G  K  G  L  E  W  V  A] [E   I  R  L  K  S  D  N  Y  A  T    -
                             204  205
     CATTATGCGGAGTCTGTGAAGGGCAAATTCACCATCTCAAGAGATGATTCAAAATCTAGA
181  ------------+---------+----+----+---------+---------+---------+ 240
     GTAATACGCCTCAGACACTTCCCGTTTAAGTGGTAGAGTTCTCTACTAAGTTTTAGATCT

A    H  Y  A  E  S  V  K  G] [K  F  T  I  S  R  D  D  S  K  S  R    -

CTGTATCTGCAAATGAACAGCCTGAAAACCGAGGACACAGCCGTGTATTACTGTACAGAT
241  ------------+---------+---------+---------+---------+---------+ 300
     GACATAGACGTTTACTTGTCGGACTTTTGGCTCCTGTGTCGGCACATAATGACATGTCTA
                          FR3
A    L  Y  L  Q  M  N  S  L  K  T  E  D  T  A  V  Y  Y  C  T  D]   -
    300  301 309  310                333
        [TTCATAGACTGGGGCCAGGGAACACTAGTCACCGTCTCCTCAGCCTCCACCAAGGGCCCA
301  ---+--------+-+--------+---------+--+------+---------+---------+ 360
        [AAGTATCTGACCCCGGTCCCTTGTGATCAGTGGCAGAGGAGTCGGAGGTGGTTCCCGGGT
            CDR3            FR4                       CONSTANT REGION
A    [F  I  D] [W  G  Q  G  T  L  V  T] [V  S  S  A  S  T  K  G  P    -

TCGGTCTTCCCCCTGGCACCCTCCTCCAAGAGCACCTCTGGGGGCACAGCGGCCCTGGGC
361  ------------+---------+---------+---------+---------+---------+ 420
     AGCCAGAAGGGGGACCGTGGGAGGAGGTTCTCGTGGAGACCCCCGTGTCGCCGGGACCCG

A    S  V  F  P  L  A  P  S  S  K  S  T  S  G  G  T  A  A  L  G    -

TGCCTGGTCAAGGACTACTTCCCCGAACCGGTGACGGTGTCGTGGAACTCAGGCGCCCTG
421  ------------+---------+---------+---------+---------+---------+ 480
     ACGGACCAGTTCCTGATGAAGGGGCTTGGCCACTGCCACAGCACCTTGAGTCCGCGGGAC

A    C  L  V  K  D  Y  F  P  E  P  V  T  V  S  W  N  S  G  A  L    -

ACCAGCGGCGTGCACACCTTCCCGGCTGTCCTACAGTCCTCAGGACTCTACTCCCTCAGC
481  ------------+---------+---------+---------+---------+---------+ 540
     TGGTCGCCGCACGTGTGGAAGGGCCGACAGGATGTCAGGAGTCCTGAGATGAGGGAGTCG

A    T  S  G  V  H  T  F  P  A  V  L  Q  S  S  G  L  Y  S  L  S    -

AGCGTGGTGACCGTGCCCTCCAGCAGCTTGGGCACCCAGACCTACATCTGCAACGTGAAT
541  ------------+---------+---------+---------+---------+---------+ 600
     TCGCACCACTGGCACGGGAGGTCGTCGAACCCGTGGGTCTGGATGTAGACGTTGCACTTA

A    S  V  V  T  V  P  S  S  S  L  G _T  Q  T  Y  I  C  N  V  N    -

CACAAGCCCAGCAACACCAAGGTGGACAAGAAAGTGGAGCCCAAATCTTGTGACAAAACT
601  ------------+---------+---------+---------+---------+---------+ 660
     GTGTTCGGGTCGTTGTGGTTCCACCTGTTCTTTCACCTCGGGTTTAGAACACTGTTTTGA

A    H  K  P  S  N  T  K  V  D  K  K  V  E  P  K  S  C  D  K  T    -

CACACATGCCCACCGTGCCCAGCACCTGAACTCGCGGGGCACCGTCAGTCTTCCTCTTC
661  ------------+---------+---------+---------+---------+---------+ 720
```

```
                GTGTGTACGGGTGGCACGGGTCGTGGACTTGAGCGCCCCGTGGCAGTCAGAAGGAGAAG
A               H  T  C  P  P  C  P  A  P  E  L  A  G  A  P  S  V  F  L  F   -

CCCCCAAAACCCAAGGACACCCTCATGATCTCCCGGACCCCTGAGGTCACATGCGTGGTG
        721     ---------+---------+---------+---------+---------+---------+ 780
                GGGGGTTTTGGGTTCCTGTGGGAGTACTAGAGGGCCTGGGGACTCCAGTGTACGCACCAC

A               P  P  K  P  K  D  T  L  M  I  S  R  T  P  E  V  T  C  V  V   -

GTGGACGTGAGCCACGAAGACCCTGAGGTCAAGTTCAACTGGTACGTGGACGGCGTGGAG
        781     ---------+---------+---------+---------+---------+---------+ 840
                CACCTGCACTCGGTGCTTCTGGGACTCCAGTTCAAGTTGACCATGCACCTGCCGCACCTC

A               V  D  V  S  H  E  D  P  E  V  K  F  N  W  Y  V  D  G  V  E   -

GTGCATAATGCCAAGACAAAGCCGCGGGAGGAGCAGTACAACAGCACGTACCGTGTGGTC
        841     ---------+---------+---------+---------+---------+---------+ 900
                CACGTATTACGGTTCTGTTTCGGCGCCCTCCTCGTCATGTTGTCGTGCATGGCACACCAG

A               V  H  N  A  K  T  K  P  R  E  E  Q  Y  N  S  T  Y  R  V  V   -

AGCGTCCTCACCGTCCTGCACCAGGACTGGCTGAATGGCAAGGAGTACAAGTGCAAGGTC
        901     ---------+---------+---------+---------+---------+---------+ 960
                TCGCAGGAGTGGCAGGACGTGGTCCTGACCGACTTACCGTTCCTCATGTTCACGTTCCAG

A               S  V  L  T  V  L  H  Q  D  W  L  N  G  K  E  Y  K  C  K  V   -

TCCAACAAAGCCCTCCCAGCCCCCATCGAGAAAACCATCTCCAAAGCCAAAGGGCAGCCC
        961     ---------+---------+---------+---------+---------+---------+ 1020
                AGGTTGTTTCGGGAGGGTCGGGGGTAGCTCTTTTGGTAGAGGTTTCGGTTTCCCGTCGGG

A               S  N  K  A  L  P  A  P  I  E  K  T  I  S  K  A  K  G  Q  P   -

CGAGAACCACAGGTGTACACCCTGCCCCCATCCCGGGATGAGCTGACCAAGAACCAGGTC
        1021    ---------+---------+---------+---------+---------+---------+ 1080
                GCTCTTGGTGTCCACATGTGGGACGGGGGTAGGGCCCTACTCGACTGGTTCTTGGTCCAG

A               R  E  P  Q  V  Y  T  L  P  P  S  R  D  E  L  T  K  N  Q  V   -

AGCCTGACCTGCCTGGTCAAAGGCTTCTATCCCAGCGACATCGCCGTGGAGTGGGAGAGC
        1081    ---------+---------+---------+---------+---------+---------+ 1140
                TCGGACTGGACGGACCAGTTTCCGAAGATAGGGTCGCTGTAGCGGCACCTCACCCTCTCG

A               S  L  T  C  L  V  K  G  F  Y  P  S  D  I  A  V  E  W  E  S   -

AATGGGCAGCCGGAGAACAACTACAAGACCACGCCTCCCGTGCTGGACTCCGACGGCTCC
        1141    ---------+---------+---------+---------+---------+---------+ 1200
                TTACCCGTCGGCCTCTTGTTGATGTTCTGGTGCGGAGGGCACGACCTGAGGCTGCCGAGG

A               N  G  Q  P  E  N  N  Y  K  T  T  P  P  V  L  D  S  D  G  S   -

TTCTTCCTCTACAGCAAGCTCACCGTGGACAAGAGCAGGTGGCAGCAGGGGAACGTCTTC
        1201    ---------+---------+---------+---------+---------+---------+ 1260
                AAGAAGGAGATGTCGTTCGAGTGGCACCTGTTCTCGTCCACCGTCGTCCCCTTGCAGAAG

A               F  F  L  Y  S  K  L  T  V  D  K  S  R  W  Q  Q  G  N  V  F   -

TCATGCTCCGTGATGCATGAGGCTCTGCACAACCACTACACGCAGAAGAGCCTCTCCCTG
        1261    ---------+---------+---------+---------+---------+---------+ 1320
                AGTACGAGGCACTACGTACTCCGAGACGTGTTGGTGATGTGCGTCTTCTCGGAGAGGGAC

A               S  C  S  V  M  H  E  A  L  H  N  H  Y  T  Q  K  S  L  S  L   -

TCTCCGGGTAAATGA
        1321    ---------+----- 1335
                AGAGGCCCATTTACT

ANTIBODIES TO CD23, DERIVATIVES THEREOF, AND THEIR THERAPEUTIC USES

This is a national stage application of PCT/GB99/01434, filed on May 7, 1999 under 35 U.S.C. 371, designating the United States and published in English.

The present invention relates to antibodies which bind to the CD23 (FCεRII) type II molecule particularly altered antibodies, the preparation of such antibodies, pharmaceutical compositions which contain such antibodies and their use in therapy.

CD23 (FCERII) is a type II molecule of the C-lectin family which also includes the lymphocyte homing receptor (MEL-14) and the endothelial leukocyte adhesion molecule-1 (ELAM-1). It is a low affinity receptor for IgE. In humans a variety of haematopoietic cell types express CD23 on their surface, including follicular dendritic cells, B cells, T cells and macrophages. CD23 molecules are also found in soluble forms in biological fluids. Soluble CD23 (sCD23) molecules are formed by proteolytic cleavage of transmembrane receptors. CD23 has pleiotropic activities including mediation of cell adhesion, regulation of IgE and histamine release, rescue of B cells from apoptosis and regulation of myeloid cell growth. These functional activities are mediated through the binding to specific ligands of cell-associated CD23, or sCD23, the latter acting in a cytokine-like manner (Conrad, D. H., Annu Rev Immunol 8, 623–645 1990); Delespesse, G., et al., Adv Immunol 49, 149–191 (1991); Bonnefoy, J. Y., et al., Curr Opin Immunol 5, 94447 (1993).

Increased expression of CD23 has been observed in a number of inflammatory diseases. CD23 has been identified in synovial biopsies from patients with chronic synovitis, and sCD23 can be measured at concentrations exceeding the normal range in the serum and synovial fluid of patients with rheumatoid arthritis (Bansal, A. S., Oliver, W., Marsh, M. N., Pumphrey, R. S., and Wilson, P. B., Immunology 79, 285–289 (1993); Hellen, E. A., Rowlands, D. C., Hansel, T. T., Kitas, G. D., and Crocker, J. J., Clin Pathol 44, 293–296 (1991); Chomarat, P., Brioloay, J., Banchereau, J., & Miossec, P., Arthritis Rheum 86, 234–242 (1993); Bansal, A., et al., Clin Exp Immunol 89, 452–455 (1992); Rezonzew, R., & Newkirk, M. N., Clin Immunol Immunopathol 71, 156–163 (1994). In addition, levels of serum sCD23 in rheumatoid arthritis patients are related to disease status and correlate with serum rheumatoid factor (Bansal, A. S., et al., Clin Exp Rheumatol 12, 281–285 (1994). Pro-inflammatory cytokines appear to be particularly important in rheumatoid arthritis, and a central role for TNF-a and IL-1b in the destruction of arthritic joints has been postulated (Brennan, F. M., Chantry, D., Jackson, A., Maini, R., & Feldman, M., Lancet 2, 244–247 (1989); Brennan, F. M., Maini, R. M., & Feldman M., Br J Rheumatol 31, 293–298 (1992).

Antibodies typically comprise two heavy chains linked together by disulphide bonds and two light chains. Each light chain is linked to a respective heavy chain by disulphide bonds. Each heavy chain has at one end a variable domain followed by a number of constant domains. Each light chain has a variable domain at one end and a constant domain at its other end. The light chain variable domain is aligned with the variable domain of the heavy chain. The light chain constant domain is aligned with the first constant domain of the heavy chain. The constant domains in the light and heavy chains are not involved directly in binding the antibody to antigen.

The variable domains of each pair of light and heavy chains form the antigen binding site. The domains on the light and heavy chains have the same general structure and each domain comprises a framework of four regions, whose sequences are relatively conserved, connected by three complementarity determining regions (CDRs). The four framework regions largely adopt a beta-sheet conformation and the CDRs form loops connecting, and in some cases forming part of, the beta-sheet structure. The CDRs are held in close proximity by the framework regions and, with the CDRs from the other domain, contribute to the formation of the antigen binding site. CDRs and framework regions of antibodies may be determined by reference to Kabat et al ("Sequences of proteins of immunological interest" US Dept. of Health and Human Services, US Government Printing Office, 1987).

The preparation of altered antibodies which the variable region of a rodent antibody is combined with the constant region of a human antibody is now well established in the art (Oi and Morrison (1986) Biotechniques 4, 214–212). Humanised antibodies in which the CDRs are derived from a source different from that of the framework of the antibody's variable domains are disclosed in EP-A-0239400. The CDRs may be derived from a rodent or primate monoclonal antibody. The framework of the variable domains, and the constant domains, of the antibody are usually derived from a human antibody. Such altered antibodies should not elicit as great an immune response when administered to a human compared to the immune response mounted by a human against a wholly foreign antibody such as one derived from a rodent.

Murine monoclonal antibodies have been raised against the CD23 receptor (FCεRII) (PCT/EP/95/04109). However, such monoclonal antibodies are not ideal for human therapy as they are potentially immunogenic when injected into a human patient and may be lytic. Furthermore commercially available antibodies which bind to the CD23 receptor recognise distinct epitopes expressed on the CD23 receptor; epitope binding specificity can play a significant part in the efficacy of an antibody for a particular purpose. Moreover, selection of antibodies with high affinity for the target receptor can be therapeutically advantageous as the dose required will be lower than for a monoclonal with less affinity for the same receptor.

According to the present invention, there is provided an altered antibody which comprises sufficient of the amino acid sequence of each CDR shown below that the antibody is capable of binding to the CD23 (FCεRII) type II molecule expressed on haematopoietic cells:

```
light chain

RSSKSLLY KDGKTYLN      CDRL1 (SEQ ID NO: 3)
LMSTRAS . . .          CDRL2 (SEQ ID NO: 5)
QQLVEYPFT              CDRL3 (SEQ ID NO: 7)
heavy chain GYWMS . . .            CDRH1 (SEQ ID NO: 9)
EIRLKSDNYATHYAESVKG    CDRH2 (SEQ ID NO: 11)
FID . . .              CDRH3 (SEQ ID NO: 13)
```

The present invention also relates to an antibody which binds to the same epitope as an antibody having the CDRs described above. Competitive inhibition assays are used for mapping of the epitopes on an antigen such as the CD23 molecule. For example FACS competition analysis involves the use of cells expressing the molecule as a target, the test antibody is labelled with one fluorochrome and a second antibody known to bind to the same antigen is labelled with a second differently coloured fluorochrome. If both fluorochromes are present the antibodies do not competitively inhibit each other and are therefore deemed to recognise separate epitopes on the target molecule. Epitope mapping can also be undertaken using direct peptide library binding assays in which peptide sequences from a target antigen are expressed on pins and screened using flourochrome-labelled antibodies as before. In epitope mapping studies the antibody having the CDRs described above has been shown to define a novel epiotpe on the CD23 molecule. The invention therefore provides an antibody which competitively inhibits the binding of an antibody having the CDR sequences set out above to the CD23 (FCεRII) type II molecule expressed on haematopoietic cells.

An antibody according to the invention is preferably altered, it may be a chimaeric antibody which comprises sufficient of the variable heavy and light chain sequences of the murine antibody C11 set out in FIGS. 1 and 2 (SEQ ID 1 and 2 and SEQ ID 46, 47, 50 and 51) such that it is capable of binding to the CD23 molecule, and a human constant region. The antibody may be a chimaeric antibody of the type described in WO 86/01533 which comprises an antigen binding region and a non-immunoglobulin region. The antigen binding region is an antibody light chain variable domain and/or heavy chain variable domain. Typically the chimaeric antibody comprises both light and heavy chain variable domains. The non-immunoglobulin region is fused to the C-terminus of the antigen binding region. The non-immunoglobulin region is typically a non-immunoglobulin protein and may be an enzyme region derived from a protein having known binding specificity, from a protein toxin or indeed from any protein expressed by a gene. The non-immunoglobulin region may be a carbohydrate region. The two regions of the chimaeric antibody may be connected via a cleavable linker sequence. The altered antibody may also be a bi-specific antibody.

The altered antibody may be a humanised antibody in which sufficient of one or more of the amino acid sequences of each CDR (and if necessary framework residues), is present in human frameworks such that it is capable of binding to the CD23 molecule.

Suitably, the CDRs of an antibody according to the invention are the light chain CDRs L1 to L3 and the heavy chain CDRs H1 to H3 above. The amino acid sequences of these CDRs may be changed, however. The amino acid sequence of each CDR may be changed by amino acid substitutions, insertions and/or deletions.

Each CDR may therefore include one or two amino acid substitutions, insertions and/or deletions. There may be up to three amino acid substitutions, insertions and/or deletions in light chain CDRL3 or heavy chain CDRH3. Up to four amino acid substitutions, insertions and/or deletions may be present in light chain CDRL1. Up to six amino acid substitutions, insertions and/or deletions may be present in heavy chain CDRH2. Preferably the amino acid sequence of each CDR is substantially homologous to that of each CDR set out above.

Preferably the degree of sequence identity is at least 50% and more preferably it is at least 75%. Sequence identities of at least 90% or of at least 95% are most preferred.

It will nevertheless be appreciated by the skilled person that high degrees of sequence identity are not necessarily required since various amino acids may often be substituted for other amino acids which have similar properties without substantially altering or adversely affecting certain properties of a protein. These are sometimes referred to as "conservative" amino acid changes. Thus the amino acids glycine, valine, leucine or isoleucine can often be substituted for one another. Other amino acids which can often be substituted for one another include: phenylalanine, tyrosine and tryptophan (amino acids having aromatic side chains); lysine, arginine and histidine (amino acids having basic side chains); aspartate and glutamate (amino acids having acidic side chains); asparagine and glutamine (amino acids having amide side chains) and cysteine and methionine (amino acids having sulphur containing side chains). Thus the term "derivative" can also include a variant of an amino acid sequence comprising one or more such "conservative" changes relative to said sequence.

The framework and the constant domains of the antibody are preferably human framework and human constant domains. Preferably the framework of the variable region of the antibody heavy chain is substantially homologous to the corresponding framework of the human protein KOL (Schmidt et al, Hoppe-Seyler's Z. Physiol. Chem., 364 713–747, 1983). Homology in respect of the framework is generally 80% or more with respect to KOL, for example 90% or more or 95% or more. Furthermore, the seventh residue of framework 4 in KOL is suitably Thr or Leu, preferably Leu. This residue is KOL residue 109 by Kabat et al, 1987. A number of amino acid substitutions, insertions and/or deletions may be present. For example, one or more of the residues at position 49, 66, 76, 77 and 94 may be altered to the equivalent residue in the murine antibody. Other candidate framework changes that may be made to restore binding include amino acid residues 27, 30, 48, 67, 71, 91 and 93. The amino acid numbering is according to Kabat et al supra.

The framework of the variable region of the antibody light chain is typically substantially homologous to the variable domain framework of the protein HSIGKVII (SEQ ID NO:54, EMBL data base: Klobeck, H. G., EMBL data library submitted Apr. 7, 1986). There is a frameshift in this sequence at position 452. To rectify the reading frame, a deletion of base 452 (T) is made.

Homology in respect of the framework is generally 80% or more with respect to the chosen sequence, for example 90% or more or 95% or more. A number of amino acid substitutions, insertions and/or deletions may be present, for example at amino acid residue 64 but also or instead at 71 according to the numbering of Kabat et al., The invention also provides an antibody which comprises the variable heavy and light chain sequences set out in FIGS. 3 and 4 (SEQ IDS 17 and 18).

The antibody preferably has the structure of a natural antibody or a fragment thereof. The antibody may therefore comprise a complete antibody, a (Fab')$_2$ fragment, a Fab fragment, a light chain dimer or a heavy chain dimer. The antibody may be an IgG such as IgG1, IgG2, IgG3 or IgG4; or IgM, IgA, IgE or IgD or a modified variant thereof. The constant domain of the antibody heavy chain may be selected accordingly. The light chain constant domain may be a kappa or lambda constant domain.

The constant region is selected according to the functionality required. Normally an IgG1 will demonstrate lytic ability through binding to complement and will mediate ADCC (antibody dependent cell cytotoxicity). An IgG4 will be preferred if an non-cytotoxic blocking antibody is required. However, IgG4 antibodies can demonstrate instability in production and therefore is may be more preferable to modify the generally more stable IgG1. Suggested modifications are described in EP0307434 preferred modifications include at positions 235 and 237. The invention therefore provides a lytic or a non-lytic form of an antibody according to the invention.

Each chain of the antibody may be prepared by CDR replacement. The CDRs of a variable region of a light or heavy chain of a human antibody are replaced by sufficient of the amino acid sequence of each CDR of the anti-CD23 antibody that the resulting antibody is capable of binding to the CD23 molecule. The CDR-encoding regions of DNA encoding a hypervariable region of a human antibody chain are replaced by DNA encoding the desired CDRs. If appropriate, this altered DNA is linked to DNA encoding a constant domain for the antibody chain. The DNA is cloned into an expression vector. The expression vector is introduced into a compatible host cell which is cultured under such conditions that the antibody chain is expressed. Complementary antibody chains which are co-expressed in this way may then assemble to form the humanised antibody.

There are four general steps to humanise a monoclonal antibody. These are:
(1) determining the nucleotide and predicted amino acid sequence of the starting antibody light and heavy variable domains;
(2) designing the humanised antibody, i.e. deciding which antibody framework region to use during the humanising process;
(3) the actual humanising methodologies/techniques; and
(4) the transfection and expression of the humanised antibody.

The invention therefore provides a DNA sequence encoding an antibody chain which comprises one or more of the sequences according to:

```
CDRL1 base pair numbers 70-117 of   (SEQ ID NOS: 4)
FIG. 3
CDRL2 base pair numbers 163-183 of  (SEQ ID NOS: 6)
FIG. 3
CDRL3 base pair numbers 280-306 of  (SEQ ID NOS: 8)
FIG. 3
CDRH1 base pair numbers 91-105 of   (SEQ ID NOS: 10)
FIG. 4
CDRH2 base pair numbers 148-204 of  (SEQ ID NOS: 12)
FIG. 4
CDRH3 base pair numbers 301-309 of  (SEQ ID NOS: 14)
FIG. 4
``` or a DNA sequence encoding an antibody chain which comprises one or both of the sequences according to FIG. 3 or 4 (SEQ ID NOS: 17 or 18 and SEQ ID NOS 48 and 49).

Step 1: Determining the Nucleotide and Predicted Amino Acid Sequence of the Antibody Light and Heavy Chain Variable Domains To humanise an antibody only the amino acid sequence of antibody's heavy and light chain variable domains needs to be known. The sequence of the constant domains is irrelevant because these do not contribute to the reshaping strategy. The simplest method of determining an antibody's variable domain amino acid sequence is from cloned cDNA encoding the heavy and light chain variable domain.

There are two general methods for cloning a given antibody's heavy and light chain variable domain cDNAs: (1) via a conventional cDNA library, or (2) via the polymerase chain reaction (PCR). Both of these methods are widely known. Given the nucleotide sequence of the cDNAs, it is a simple matter to translate this information into the predicted amino acid sequence of the antibody variable domains. In the present instance, the nucleotide sequence and predicted amino acid sequence of the rodent C11 antibody chains are shown in FIGS. 1 and 2 (SEQ ID NOS: 1 (heavy) and 2 (light) and SEQ ID NOS 46 and 47).

Step 2: Designing the Humanised Antibody

There are several factors to consider in deciding which human antibody sequence to use during the humanisation. The humanisation of light and heavy chains are considered independently of one another, but the reasoning is basically similar for each.

This selection process is based on the following rationale: a given antibody's antigen specificity and affinity is primarily determined by the amino acid sequence of the variable region CDRs. Variable domain framework residues have little or no direct contribution. The primary function of the framework regions is to hold the CDRs in their proper spatial orientation to recognise antigen. Thus the substitution of rodent CDRs into a human variable domain framework is most likely to result in retention of their correct spatial orientation if the human variable domain framework is highly homologous to the rodent variable domain from which they originated. A human variable domain should preferably be chosen therefore that is highly homologous to the rodent variable domain(s).

A suitable human antibody variable domain sequence can be selected as follows:

1. Using a computer program, search all available protein (and DNA) databases for those human antibody variable domain sequences that are most homologous to the rodent antibody variable domains. The output of a suitable program is a list of sequences most homologous to the rodent antibody, the percent homology to each sequence, and an alignment of each sequence to the rodent sequence. This is done independently for both the heavy and light chain variable domain sequences. The above analyses are more easily accomplished if only human immunoglobulin sequences are included.
2. List the human antibody variable domain sequences and compare for homology. Primarily the comparison is performed on length of CDRs, except CDR3 of the heavy chain which is quite variable. Human heavy chains and Kappa and Lambda light chains are divided into subgroups; Heavy chain 3 subgroups, Kappa chain 4 subgroups, Lambda chain 6 subgroups. The CDR sizes within each subgroup are similar but vary between subgroups. It is usually possible to match a rodent antibody CDR to one of the human subgroups as a first approximation of homology. Antibodies bearing CDRs of similar length are then compared for amino acid sequence homology, especially within the CDRs, but also in the surrounding framework regions. The human variable domain which is most homologous is chosen as the framework for humanisation.

Step 3: The Actual Humanising Methodologies/Techniques

An antibody may be humanised by grafting the desired CDRs onto a human framework according to EP-A-0239400. A DNA sequence encoding the desired reshaped antibody can therefore be made beginning with the human DNA whose CDRs it is wished to reshape. The rodent variable domain amino acid sequence containing the desired CDRs is compared to that of the chosen human antibody variable domain sequence. The residues in the human variable domain are marked that need to be changed to the corresponding residue in the rodent to make the human variable region incorporate the rodent CDRs. There may also be residues that need substituting in, adding to or deleting from the human sequence.

Oligonucleotides are synthesised that can be used to mutagenise the human variable domain framework to contain the desired residues. Those oligonucleotides can be of any convenient size. One is normally only limited in length by the capabilities of the particular synthesiser one has available. The method of oligonucleotide-directed in vitro mutagenesis is well known.

Alternatively, humanisation may be achieved using the recombinant polymerase chain reaction (PCR) methodology of WO92/07075. Using this methodology, a CDR may be spliced between the framework regions of a human antibody.

In general, the technique of WO92/07075 can be performed using a template comprising two human framework regions, AB and CD, and between them, the CDR which is to be replaced by a donor CDR. Primers A and B are used to amplify the framework region AB, and primers C and D used to amplify the framework region CD. However, the primers B and C each also contain, at their 5' ends, an additional sequence corresponding to all or at least part of the donor CDR sequence. Primers B and C overlap by a length sufficient to permit annealing of their 5' ends to each other under conditions which allow a PCR to be performed. Thus, the amplified regions AB and CD may undergo gene splicing by overlap extension to produce the humanised product in a single reaction.

Step 4: The Transfection and Expression of the Reshaped Antibody

Following the mutagenesis reactions to reshape the antibody, the mutagenised DNAs can be linked to an appropriate DNA encoding a light or heavy chain constant region, cloned into an expression vector, and transfected into host cells, preferably mammalian cells. These steps can be carried out in routine fashion. A reshaped antibody may therefore be prepared by a process comprising:

(a) preparing a first replicable expression vector including a suitable promoter operably linked to a DNA sequence which encodes at least a variable domain of an Ig heavy or light chain, the variable domain comprising framework regions from a human antibody and the CDRs required for the humanised antibody of the invention;
(b) preparing a second replicable expression vector including a suitable promoter operably linked to a DNA sequence which encodes at least the variable domain of a complementary Ig light or heavy chain respectively;
(c) transforming a cell line with the first or both prepared vectors; and
(d) culturing said transformed cell line to produce said altered antibody.

Preferably the DNA sequence in step (a) encodes both the variable domain and the or each constant domain of the human antibody chain. The humanised antibody can be recovered and purified. The cell line which is transformed to produce the altered antibody may be a Chinese Hamster Ovary (CHO) cell line or an immortalised mammalian cell line, which is advantageously of lymphoid origin, such as a myeloma, hybridoma, trioma or quadroma cell line. The cell line may also comprise a normal lymphoid cell, such as a B-cell, which has been immortalised by transformation with a virus, such as the Epstein-Barr virus. Most preferably, the immortalised cell line is a myeloma cell line or a derivative thereof. The expression system of choice is the glutamine synthetase expression system described in WO87/04462.

Although the cell line used to produce the humanised antibody is preferably a mammalian cell line, any other suitable cell line, such as a bacterial cell line or a yeast cell line, may alternatively be used. For single antibody chains, it is envisaged that E. coli—derived bacterial strains could be used. The antibody obtained is checked for functionality. If functionality is lost, it is necessary to return to step (2) and alter the framework of the antibody.

The invention therefore provides an expression vector comprising DNA encoding and adapted for the expression of an antibody according to the invention and host cells transformed with said expression vectors.

Once expressed, the whole antibodies, their dimers, individual light and heavy chains, or other immunoglobulin forms of the present invention can be purified according to standard procedures of the art, including ammonium sulfate precipitation, affinity columns, column chromatography, gel electrophoresis and the like (see, generally, Scopes, R., *Protein Purification*, Springer-Verlag, N.Y. (1982)). Substantially pure immunoglobulins of at least about 90 to 95% homogeneity are preferred, and 98 to 99% or more homogeneity most preferred, for pharmaceutical uses. Once purified, partially or to homogeneity as desired, a an antibody may then be used therapeutically or in developing and performing assay procedures, immunofluorescent stainings, and the like (See, generally, *Immunological Methods*, Vols. I and II, Lefkovits and Pernis, eds., Academic Press, New York, N.Y. (1979 and 1981)).

The antibody may function by blocking the interaction between membrane bound CD23 and a ligand which binds to it. In vitro assays e.g. radio-immune assays may be used to study such a blocking effect. The antibody may also function by binding to soluble CD23. Membrane bound CD23 is known to undergo cleavage from the cell surface leading to the formation of a number of soluble fragments. These fragments act like cytokines and play a major role in IgE formation. Excessive levels of soluble CD23 have therefore been implicated in disease. By binding to these fragments the antibodies according to the invention can interfere with the ability of the soluble CD23 to mediate its effects. The antibodies according to the invention are also believed to prevent soluble CD23 production by preventing cleavage of the membrane bound receptor. The invention therefore provides the use of an anti-CD23 antibody in the manufacture of a medicament for blocking soluble CD23 formation.

The ability of any antibody to mediate its effect will be related to its affinity for the target antigen. Antibodies according to the invention have a very high affinity for the CD23 receptor. The affinity constant of such antibodies is preferably greater than $1 \times 10^9$ Ka Mol$^{-1}$ and more preferably greater than $1 \times 10^{10}$ Ka Mol$^{-1}$. This invention therefore provides antibodies capable of binding the CD23 receptor or soluble CD23 characterised by an affinity constant equal to or greater than $1 \times 10^9$ Ka Mol$^{-1}$.

Antibodies which bind to the CD23 receptor can be used in vivo in the treatment or prophylaxis of inflammatory or autoimmune diseases. This is of great significance given the fact that many of these diseases are difficult or impossible to treat effectively, despite long standing research into their research into their nature causes. This is particularly the case in respect of arthritis, which often affects people in middle age and can cause them to give up work prematurely. An effective treatment of arthritis has been a long standing goal of many research groups.

The antibodies of the present invention are believed to be useful in the treatment or prophylaxis of several diseases including arthritis, lupus erythematosus, Hashimotos thyroiditis, multiple sclerosis, diabetes, uveitis, dermatitis, psoriasis, urticaria, nephrotic syndrome, glomerulonephritis, inflammatory bowel disease, ulcerative colitis, Crohn's disease, sjogren's syndrome, allergies, asthma more specifically, allergic or intrinsic asthma, acute asthmatic exacerbation, rhinitis, eczema, GVH, COPD, insulitis, bronchitis (particularly chronic bronchitis) or diabetes (particularly Type 1 diabetes).

The present invention therefore provides the use of an antibody according to the invention in the manufacture of a medicament for the treatment of any one or more of the above disorders. The invention also provides a method for the treatment of one or more of the above disorders comprising the administration of a therapeutically effective dose of an antibody according to the invention.

Antibodies according to the invention may also be useful in studying the interactions between CD23 and various ligands e.g. between CD23 and CD21, between CD23 and CD11b, between CD23 and CD11c, between CD23 and an 80 to 85 KDa endothelial cell protein (which may be an 80 or 85 KDa endothelial cell protein) or between CD23 and a 115 KDa protein (which is believed to be related to the 80 to 85 KDa endothelial protein). One or more of the above interactions are believed to occur in vivo. Antibodies or other binding agents which are capable of blocking these interactions are particularly preferred since it is believed that they may be especially suitable for reducing or alleviating cytokine mediated inflammatory effects. They may be useful against B-cell malignancies such as chronic lymphocytic leukaemia, and hairy cell leukaemia.

An alternative mechanism of action of anti CD23 therapy could involve the blocking of an IgE immune response.

Antibodies of this invention are also of particular use in the treatment of prophylaxis of allergic diseases, including non-IgE mediated diseases. They may be used in the treatment and prophylaxis of ulcerative colitis. They may also be used in the treatment and prophylaxis of Crohn's disease.

The antibodies of the present invention may be used alone or in combination with immunosuppressive agents such as steroids, cyclosporin, or antibodies such as an anti-lymphocyte antibody or more preferably with a tolerance-inducing, anti-autoimmune or anti-inflammatory agent such as a CD4+ T cell inhibiting agent e.g. an anti-CD4 antibody (preferably a blocking or non-depleting antibody), an anti-CD8 antibody, a TNF antagonist e.g. an anti-TNF antibody or TNF inhibitor e.g. soluble TNF receptor, or agents such as NSAIDs.

Suitable dosages of the substance of the present invention will vary, depending upon factors such as the disease or disorder to be treated, the route of administration and the age and weight of the individual to be treated.

Without being bound by any particular dosages, it is believed that for instance for parenteral administration, a daily dosage of from 0.01 to 20 mg/kg of a antibody of the present invention (usually present as part of a pharmaceutical composition as indicated above) may be suitable for treating a typical adult. More suitably the dose might be 0.1 to 5 mg/kg, such as 0.1 to 2 mg/kg. A unit dose suitably be will be 1400 mg.

The antibodies can also be used as separately administered compositions given in conjunction with chemotherapeutic or immunosuppressive agents. Typically, the agents will include cyclosporin A or a purine analog (e.g., methotrexate, 6-mercaptopurine, or the like), but numerous additional agents (e.g., cyclophosphamide, prednisone, etc.) well-known to those skilled in the art may also be utilised.

If it is desired to lyse the cells to which the antibody binds, an antibody of the present invention may form part of an immunotoxin. Immunotoxins are characterised by two components and are particularly useful for killing selected cells in vitro or in vivo. One component is a cytotoxic agent which is usually fatal to a cell when attached or absorbed. The second component, known as the "delivery vehicle", provides a means for delivering the toxic agent to a particular cell type, such as cells comprising a carcinoma. The two components are commonly chemically bonded together by any of a variety of well-known chemical procedures. For example, when the cytotoxic agent is a protein and the second component is an intact immunoglobulin, the linkage may be by way of heterobifunctional cross-linkers, eg., SPDP, carbodiimide, glutaraldehyde, or the like. Production of various immunotoxins is well-known within the art, and can be found, for example in "Monoclonal Antibody-Toxin Conjugates: Aiming the Magic Bullet", Thorpe et al, *Monoclonal Antibodies in Clinical Medicine*, Academic Press, pp. 168–190 (1982).

A variety of cytotoxic agents are suitable for use in immunotoxins. Cytotoxic agents can include radionuclides, such as Iodine-131, Yttrium-90, Rhenium-188, and Bismuth-212; a number of chemotherapeutic drugs, such as vindesine, methotrexate, adriamycin, and cisplatin; and cytotoxic proteins such as ribosomal inhibiting proteins like pokeweed antiviral protein, *Pseudomonas* exotoxin A, ricin, diphtheria toxin, ricin A chain, etc., or an agent active at the cell surface, such as the phospholipase enzymes (e.g., phospholipase C). See, generally, "Chimaeric Toxins," Olsnes and Phil, *Pharmac. Ther.*, 25:335–381 (1982), and "Monoclonal Antibodies for Cancer Detection and Therapy," eds. Baldwin and Byers, pp. 159–179, 224–266, Academic Press (1985).

The delivery component of the immunotoxin is an antibody according to the present invention. Intact immunoglobulins or their binding fragments, such as Fab, are preferably used. Typically, the antibodies in the immunotoxins will be of the human IgA, IgM or IgG isotype, but other mammalian constant regions may be utilised as desired.

The invention further provides a pharmaceutical composition comprising a pharmaceutially acceptable carrier or diluent and, as active ingredient, an antibody according to the invention. The composition may comprise an immunotoxin according to the invention. The antibody, immunotoxin and pharmaceutical compositions thereof of this invention are particularly useful for parenteral administration, i.e., subcutaneously, intramuscularly or intravenously.

The compositions for parenteral administration will commonly comprise a solution of the antibody or a cocktail thereof dissolved in an acceptable carrier, preferably an aqueous carrier. A variety of aqueous carriers can be used, e.g., water, buffered water, 0.4% saline, 0.3% glycine and the like. These solutions are sterile and generally free of particulate matter. These compositions may be sterilised by conventional, well known sterilisation techniques. The compositions may contain pharmaceutically acceptable auxiliary substances as required to approximate physiological conditions such as pH adjusting and buffering agents, toxicity adjustment agents and the like, for example sodium acetate, sodium chloride, potassium chloride, calcium chloride, sodium lactate, etc. The concentration of antibody in these formulations can vary widely, for example from less than about 0.5%, usually at or at least about 1% to as much as 15 or 20% by weight and will be selected primarily based on fluid volumes, viscosities, etc., in accordance with the particular mode of administration selected.

Thus, a typical pharmaceutical composition for intramuscular injection could be made up to contain 1 ml sterile buffered water, and 50 mg of antibody. A typical composition for intravenous infusion could be made up to contain 250 ml of sterile Ringer's solution, and 150 mg of antibody. Actual methods for preparing parenterally administrable compositions will be known or apparent to those skilled in the art and are described in more detail in, for example, *Remington's Pharmaceutical Science,* 15th ed., Mack Publishing Company, Easton, Pa. (1980).

The antibodies of this invention can be lyophilised for storage and reconstituted in a suitable carrier prior to use. This technique has been shown to be effective with conventional immune globulins. Any suitable lyophilisation and reconstitution techniques can be employed. It will be appreciated by those skilled in the art that lyophilization and reconstitution can lead to varying degrees of antibody activity loss (e.g., with conventional immune globulins, IgM antibodies tend to have greater activity loss than IgG antibodies) and that use levels may have to be adjusted to compensate.

Single or multiple administrations of the compositions can be carried out with dose levels and pattern being selected by the treating physician. In any event, the pharmaceutical formulations should provide a quantity of the antibody(ies) of this invention sufficient to effectively treat the patient.

Antibodies of the present invention can further find a wide variety of utilities in vitro. By way of example, the exemplary antibodies can be utilised for T-cell typing, for isolating specific CD23 antigen bearing cells or fragments of the receptor, for vaccine preparation, or the like.

For diagnostic purposes, the antibodies may either be labelled or unlabelled. Unlabelled antibodies can be used in combination with other labelled antibodies (second antibodies) that are reactive with the humanised antibody, such as antibodies specific for human immunoglobulin constant regions. Alternatively, the antibodies can be directly labelled. A wide variety of labels may be employed, such as radionuclides, fluors, enzymes, enzyme substrates, enzyme cofactors, enzyme inhibitors, ligands (particularly haptens), etc. Numerous types of immunoassays are available and are well known to those skilled in the art.

Kits can also be supplied for use with the subject antibodies in the protection against or detection of a cellular activity or for the presence of a selected antigen. Thus, an antibody of the present invention may be provided, usually in a lyophilised form in a container, either alone or in conjunction with additional antibodies specific for the desired cell type. The antibodies, which may be conjugated to a label or toxin, or unconjugated, are included in the kits with buffers, such as Tris, phosphate, carbonate, etc., stabilisers, biocides, inert proteins, eg., serum albumin, or the like, and a set of instructions for use. Generally, these materials will be present in less than about 5% wt. based on the amount of active antibody, and usually present in total amount of at least about 0.001% wt. based again on the antibody concentration. Frequently, it will be desirable to include an inert extender or excipient to dilute the active ingredients, where the excipient may be present in from about 1 to 99% wt. of the total composition. Where a second antibody capable of binding to the chimaeric antibody is employed in an assay, this will usually be present in a separate vial. The second antibody is typically conjugated to a label and formulated in an analogous manner with the antibody formulations described above.

BRIEF DESCRIPTION OF THE DRAWINGS

FIG. 1 shows the amino acid and nucleotide sequences of the murine C11 heavy chain variable region. (SEQ ID NO: 1).

FIG. 2 shows the amino acid and nucleotide sequences of the murine C11 light chain variable region (SEQ ID NO: 2).

FIG. 3 shows the amino acid and nucleotide sequences of the humanised anti-CD23 antibody light chain variable region (SEQ ID NO:18).

FIG. 4 shows the amino acid and nucleotide sequences of the humanised anti-CD23 antibody heavy chain variable region (SEQ ID NO:17).

Figure 5:
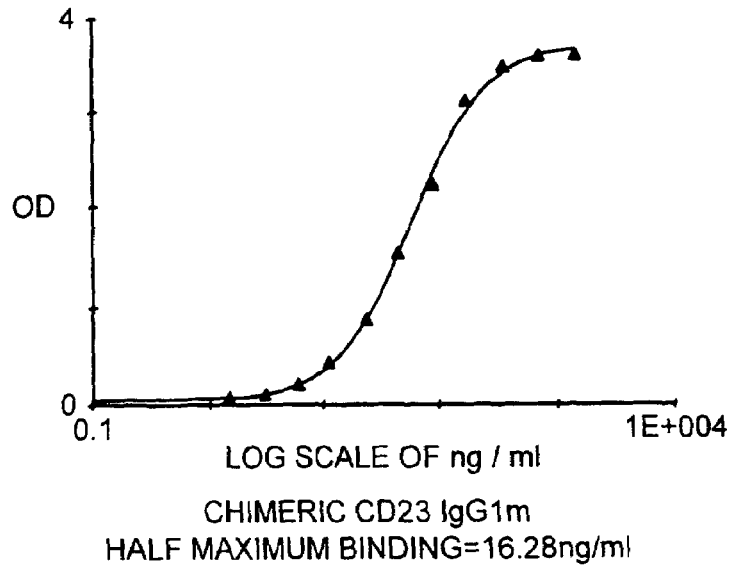
FIG. 5 shows the half maximal binding of chimaeric CD23 IgG1m

The following Examples illustrate the invention.

Cloning and Sequencing of the Murine Anti-CD23 Monoclonal Antibody

General Methodology

Unless otherwise stated, the following standard procedures and conditions were used. Manufacturers' recommended protocols were followed where applicable. Restriction digestions and other routine molecular biology procedures were performed essentially as described by Maniatis et al ("Molecular Cloning—a laboratory manual" $2^{nd}$ edition, Cold Spring Harbour Press).

PCR was performed using a programmable thermal cycler (Trio; Biometra). A typical 100 $\mu$l reaction contained 2.5 units of AmpliTaq polymerase (Perkin-Elmer-Cetus, Beaconsfield, UK) in the buffer supplied by the manufacturer; 250 $\mu$M each of dATP, dCTP, dGTP and dTTP; amplification primers at 1 $\mu$M and template DNA. Unless otherwise noted, the following cycle specifications were used:
Step 0: 95° C. for 5 minutes
Step 1: 95° C. for 1 minute
Step 2: 50° C. for 1 minute, ramping up to step 3 at 0.4° C./s
Step 3: 72° C. for 1 minute, go to step 1, repeating the loop 30 times
Step 4: 72° C. for 5 minutes DNA sequencing was performed using the dideoxy terminator method using either the Sequenase v2 system (USB, Cambridge, UK) or the fluorescent dye-terminator system (ABI).

Gel purification of DNA was performed by separation of the reaction on a low-melting point agarose gel (NuSieve GTG, FMC, Rockland, Me.). The chosen fragment was excised under UV illumination, and the DNA recovered using a Wizard PCR Preps kit (Promega, Southampton, UK).

Numbering of amino-acid residues in antibody chains follows the scheme of Kabat et al ("Sequences of proteins of immunological interest", US Dept of Health and Human Services, US Govt Printing Office, 1991).

Preparation of cDNA from C11 Hybridoma

A growing culture of C11 cells was used for RNA extraction. A culture containing $1.3 \times 10^7$ cells were centrifuged and both cell pellet and supernatant retained for analysis. The supernatant was tested for the presence of murine immunoglobulin of various isotypes by an immunological method (ISO1 kit; Sigma, Poole, UK) and the C11 monoclonal was found to be of isotype IgG1.

Messenger RNA was isolated from the cell pellet by sequential application of a Total RNA Isolation Kit (Stratagene, Cambridge, UK) (producing total RNA) and then a mRNA Purification Kit (Dynal, Oslo, Norway). Portions of both the mRNA and the total RNA were then converted to single-stranded cDNA using the Superscript Preamplification System (BRL, Paisley, Scotland, UK). Aliquots of the resulting cDNA were used in PCRs designed to separately amplify the variable regions of the C11 immunoglobulin heavy and light chains.

Cloning and Sequencing of the C11 Heavy Chain Variable Region

The heavy chain was cloned by a variation of the method of Bendig and Jones (Bio/Technology 9:88–89) in which 12 forward primers specific to the signal peptide region of the heavy chain message and 1 reverse primer specific for the mouse γ1 constant region are used in a PCR to amplify the entire variable region. Rather than add all 12 forward primers to a single reaction, 12 separate PCRs were performed, each using one of the forward primers in combination with the γ1 reverse primer. These reactions were performed with an annealing temperature of 42.5° C. (Step 2 in the scheme above).

Samples of each reaction were analysed on an agarose gel, and a band of the expected size seen only in the reaction that used the forward primer MHV11. Based on this result, two PCRs using MVH11 and the γ1 reverse primer were performed using cDNA derived from mRNA and from total RNA respectively. The use of two independent PCRs to serve as a source of material for cloning is a common device well known in the art for the avoidance of sequence errors caused by misincorporation of nucleotides by Taq polymerase.

The resulting PCR fragments were digested with XmaI and SalI, gel purified, and then cloned into pUC18. The inserts from a number of clones from each PCR were sequenced and found to be identical, suggesting that the sequence does not contain errors introduced by the PCR process. The complete sequence of the variable region is shown in FIG. 1 (SEQ ID 1), and is a perfect match to the Kabat Group IIIC heavy chain consensus.

Cloning and Sequencing of the C11 light chain variable region

The C11 light chain variable region was cloned by a similar process, again involving a set of 11 forward primers specific for the signal peptide region of the light chain message and 1 reverse primer specific for the mouse K constant region (Bendig and Jones, op cit). Additionally, as we have previously determined that this primer set does not efficiently amplify all mouse kappa light chains, we included another primer, here termed MKV12 (sequence 5' ACTAGTCGACATGMGTTTCCTTCTCAACTTCTGCTC3') (SEQ ID 41). As above, separate PCRs, each including one forward primer and the K constant reverse primer, were performed, and analysed by agarose gel electrophoresis.

Three of the reactions produced products of the expected size. These were separately digested with SalI and XmaI, purified, and cloned into pUC18 to yield clones designated VKI, VKJ and VKK. These were partially sequenced to determine their identity. Partial sequence for clone VKI was found to be identical with a known sequence, a light chain derived from the MOPC21 myeloma which has a frameshift in CDR3 (Genbank M35669), and so VKI was discarded. Partial sequence for clone VKK, including CDR3, was found to be identical with the productively rearranged MOPC21 light chain (Genbank J00560, J00552). This of itself does not preclude the VKK clone from being the correct C11 light chain as both light chains may share CDR3 in the germline configuration, but given that the myeloma parent of the hyridoma was known to be a MOPC21 derivative, and that another MOPC21 related sequence had already been identified (clone VKI), clone VKK was thought unlikely to be correct.

Clone VKJ was considered most likely to represent the true C11 light chain variable region, as the partial sequence was not identical with any sequence in Genbank. VKJ was sequenced fully, and found to be a fully-functional light chain sequence, without frameshifts, most likely using the VK167 or VK24 genes, placing it as an atypical Kabat group II sequence. The complete sequence of the VKJ clone is shown in FIG. 2 (SEQ ID 2). A second independent PCR using the primer pair that produced the VKJ clone was also performed, and the product cloned and sequenced as above to preclude the possibility that the VKJ sequence contained PCR errors. Clones from this second amplification had a sequence identical to the original VKJ clone.

Definitive proof that VKJ contained the C11 light chain variable region was obtained through the construction of a chimaeric antibody using this VK and the VH described above. This antibody was shown to bind CD23.

Designing the Chimaeric Antibody

To verify that the correct heavy and light chain variable regions had been cloned and sequenced, a chimaeric anti-CD23 was constructed. The heavy chain variable region was amplified using the clones from the cDNA library. The forward primer contained the 5' cloning site (Hind III), 5' untranslated sequence including a functional Kozac signal, together with the first six codons of the murine variable heavy region. The reverse primer engineers a Spe I site into Framework 4 in frame to fuse to a human gamma I constant region. These primers generated a 430 base pair product.

Heavy Chain Anti-CD23 Chimaeric PCR Oligos

```
5' gAT gAA gCT TTA CAg TTA CTC AgC ACA CAg gAC CTC ACC ATg gAT    SEQ ID 19
TTT ggg CTg ATT 3'
5' gAT ggA CTA gTg TCC CTT ggC CCC A 3'                           SEQ ID 20
```

The primers for amplification of the anti-CD23 light chain variable region to make chimaeric light chain were constructed containing the 5' cloning site (Hind III), 5' untranslated sequence including a functional Kozac signal, together with the first six codons of the murine variable light chain. The reverse primer contained a BsiW 1 site and anticodons for the indicated amino acids. The redundancy codes are standard: Y=T or C; K=T or G; V=A, G or C. The product was 420 base pairs.

Light Chain Anti-CD23 Chimaeric PCR Oligos

```
5' gAT gAA gCT TTA CAg TTA CTC AgC ACA CAg gAC CTC ACC ATg Agg    SEQ ID 21
TTC TCT gTT CAg 3'
5' gAT gCg TAC gTY TKA TYT CCA VCT TKG T 3'                       SEQ ID 22 (and SEQ ID
                                                                  NOS 42 to 45 and 52 and 53)
         T    R    K    I    E    L    K    T
              R              V
```

The heavy chain PCR products were cleaned, cut with Hind III and Spe I, then cloned into a pUC vector cut with Hind III and Spe I containing a human gamma I constant region. The human constant region used was the IgG1 heavy chain described in Reichmann L et al (1988) Nature 322, 323–327 but in cDNA context as described in Page, M. J. and Sydenham, M. A. (1991) Biotechnology 9, 64–68 and Crowe J. S. et al Clinical Exp Immunol (1992) 87 105.

The variable and constant region was removed from the pUC vector with Hind III and Eco RI, then cloned into the Hind III—Eco RI site of the expression vector pEE6 obtained from Celltech (Stephens & Cockett and Nucl. Acids. Res. (1989) 17, 7110).

When the heavy chain chimaeric was sequenced, 100 base pairs of 5' sequence were missing. Upon examination of the murine variable heavy chain sequence, an internal Hind III site was observed. To create the complete heavy chain variable sequence generated in the PCR products, the PCR product was digested with Hind III and the small 100 base pair fragment cloned into a Hind III digested pEE6 containing the chimaeric anti-CD23 heavy chain.

The light chain PCR products were cleaned, then cut with Hind III and BsiW 1, then ligated into a pUC vector containing the human kappa constant region.

The human kappa constant region used was as described in Reichmann et al Nature 1988 (supra). The light chain variable and constant region was removed from the pUC vector with Hind III and Eco R1. This fragment was cloned into the Hind III—Eco RI site of the expression vector pEE12 obtained from Celltech (Bebbington and Hentschel, In DNA cloning Vol 3, Chapter 8 IRL PRESS 1987).

The chimaeric heavy chain was isolated as a Bgl II—Sal I cassette and inserted at the Bam H1—Sal I site of the pEE12 light chain plasmid, such that the light and heavy chain genes were in the same plasmid.

The final expression plasmid containing the chimeric CD23 was transiently expressed in COS cells (green monkey kidney cells) as follows. Transfectam (Promega) was reconstituted to 1 mg/ml according to the recommended protocol of the manufacturer. On the day prior to transfection, $5.0 \times 10^5$ cells per well were plated in a six well plate (Costar) in a total volume of 2.5 ml of media. Medium was Dulbecco's Modified Eagle Medium (Gibco/BRL) and 10% dialysed fetal calf serum (Hyclone). The plates were incubated overnight at 37° C. For each well in the 6-well plate, 20 µl of Transfectam was added to 0.5 ml of serum free media in a sterile polystyrene bijoux container, then vortexed briefly. For each well to be transfected, 4 µg of plasmid DNA was added to the 0.5 ml of Transfectam solution in serum free media, then mixed well and left at room temperature for about 10 minutes while preparing the cells for transfection. Medium was aspirated from the cells to be transfected, then the cells were carefully rinsed 1 or 2 times with 5 ml pre-warmed serum free media per well, and then 0.5 ml of serum free media was added to each well. Previously prepared 0.5 ml DNA/Transfectam solution was added into each well and when all wells completed, the plate was gently swirled to ensure mixing. The plate was returned to the incubator for 4 hours. Two ml of complete medium (containing 1.5 times the normal serum concentration) was added to the transfection solution. The plates were returned to the incubator for three days when the medium was harvested from the plates, and assayed for antibody activity.

The chimaeric antibody bound sCD23 in an ELISA assay. For the ELISA assay to determine sCD23 binding, EIA/RIA plates (Costar) were coated with 100 µl/well of 2 µg/ml sCD23 in 35 mM $NaHCO_3$, 15 mM $Na_2CO_3$, pH 9.3 overnight at 4° C. Plates were washed three times with 150 mM NaCl, 50 mM Trizma base, 0.1% (v/v) Tween-20, pH 7.4 (TBS/Tween), blocked for 1–2 hours at 22° C. with 100 µl/well of 2% bovine serum albumin in TBS/Tween, and washed three times with TBS/Tween.

Dilutions of supernatants from the murine hybridoma C11 were added 100 µl/well on one part of the 96 well plate and dilutions of the chimaeric anti-CD23 antibody transiently expressed in the supernatants of COS cells was added to another part of the 96 well plate. The C11 murine antibody was detected with anti-mouse IgG (whole molecule) peroxidase conjugate developed in goat from Sigma A4416, diluted 1:1000 in PBS/BSA (bovine serm albumin) (1%). The chimaeric anti-CD23 antibody was detected with anti-human kappa light chain (bound and free) peroxidase conjugate, (Sigma A-7164), diluted 1:5000 in PBS/BSA (1%). Chimaeric anti-CD23 was positive for binding sCD23 in the ELISA.

The chimaeric anti-CD23 was also positive in binding membrane CD23 as determined by FACS. These data verified that the correct murine C11 heavy and light chain variable regions had been cloned and sequenced. These murine sequences were then used to develop the humanised anti-CD23 antibody.

Construction of the Humanised Heavy and Light Chain Genes

The humanised heavy and light chains were constructed following the method of Lewis and Crowe (Gene 101, 297–302,1991).

(i) Light Chain

The mouse framework variable region sequences were compared to human framework sequences in the GenBank database.

Light chain human frameworks were compared for homology to the mouse anti-human anti-CD23 light chain variable framework sequence. The framework most homologous was chosen as template for PCR overlap extension; it was:

Locus: HSIGKVII 490 bp mRNA
Definition: Human rearranged DNA for kappa-immunoglobulin leader peptide and variable region
Source: homo sapiens
Authors: Klobeck, H. G. et al. Contribution of human V kappa II germ-line genes to light chain diversity, Nature, 309, 73–76,1984.

Each amino acid that differed at the same position in the mouse and human framework was examined. The human amino acid was kept if the antigen binding is not affected because human residues should be less immunogenic than a mouse residue. The identification of specific residues that affect binding has to be hypothetical and based on data from other antibody-antigen interactions. From published data, residues 71, 91, and 94 in the heavy chain framework have been shown to interact with antigen binding (Tramontano, A., Chothia, C., and A. M. Lesk, J. Mol. Biol., 215, 175–182, 1990.; Kettleborough, C. A., Saldanha, J., Heath, V. J., Morrison, C. J. and M. M. Bendig, Protein Eng, 4, 773–783, 1991). These residues should therefore, be the same in the humanised framework as in the mouse framework. Each amino acid change is considered for size, hydrophobicity, hydrophilicity, and charge. If the human amino acid is similar to the mouse amino acid in these characteristics, then the human amino acid is used at this site.

There were 13 differences between the amino acid sequence of the mouse light chain variable framework sequence and the most homologous human variable light chain sequence. None of the mouse residues were retained. A humanised light chain variable sequence was generated and a GCG program was used to identify silent sites for the following enzymes:

AccI; HaeI; NheI; PvuII; XbaI; XhoI; XmaI

Changes in the nucleotide sequence were made to include these restriction enzyme sites without changing the amino acid sequence. The presence of these sites were included to make cutting and pasting fragments of PCR clones easier.

The humanised variable light chain was generated by grafting the mouse light chain CDRs onto an existing template (eg HSIGKVII Klobek, H. G. et al Nature (1984) 309, 73–76) containing the chosen human light chain framework sequence using splice overlap PCR. (Crowe, et al. supra.) Plasmids encoding the humanised light chain variable sequences were developed as follows:

A Kozac sequence for transcription and a signal sequence (MGWSCIILFLVATATGVHS—SEQ ID 15) is included in the light chain template sequence. A HindIII site was added at the 5' end and a Bswi I site added at the 3' end of the PCR product for cloning. The oligos for PCR overlap extension were:

was ligated into pCR™ II from "TA Cloning Kit" (Invitrogen BV, Leek, The Netherlands, product #K2000-01) following the protocol recommended by the manufacturer. Plasmid isolates were sequenced using the ABI fluorescent sequencer.

(ii) Heavy Chain

The human framework sequence most homologous to the mouse framework sequence was identified for the heavy chain. The most homologous sequence in the database for the heavy chain was:

Locus: HUMSIGVS 423 BP MRNA

Definition: Human Ig mu-chain mRNA V3b-D-J4 region 5' end

Source: Homo sapiens cDNA to mRNA

Authors: Sanz, I. et al. VH sequence of a human autoantibody. Evidence that autoantibodies can be unmutated copies of germline genes. J. Immuno. 142, 883–887, 1989.

There were seventeen differences between the amino acid sequence of the mouse heavy chain variable framework sequence and the most homologous human variable heavy chain framework sequence. In five positions 49, 66, 76, 77

```
A_L:SEQ ID NO: 23   5' gAT CAA gCT TCT CTA CAg TTA CTg AgC ACA 3'
B_L:SEQ ID NO: 24.  5' AAT CAA gTA TgT CTT CCC ATC CTT ATA CAg
                    gAg ACT CTT ACT CgA gCg ACA ggA gAT ggA ggC 3'
C_L:SEQ ID NO: 25.  5' CgC TCg AgT AAg AgT CTC CTg TAT AAg gAT ggg
                    AAg ACA TAC TTg AAT Tgg TAC CTg CAg AAg 3'
D_L:SEQ ID NO: 26.  5' TgA TgC CCg ggT ggA CAT CAA ATA gAT CAg gAg
                    CTg 3'
E_L:SEQ ID NO: 27.  5' TTg ATg TCC ACC Cgg gCA TCA ggg gTC CCT gAC
                    Agg 3'
F_L:SEQ ID NO: 28.  5' AgC CAC CTg ACg TTT gAT CTC CAC CTT ggT
                    CCC TTg
                    gCC gAA CgT gAA Tgg ATA CTC TAC CAg CTg TTg ACA gTA ATA AAC
                    CCC 3'
```

PCR reactions (Saiki et al. Science 239, 487491, 1988) were performed in a programmable heating block (Perkin Elmer, GeneAmp 9600) using 25 rounds of temperature cycling (94° C. for 1 minute, 50° C. for 2 min, and 72° C. for 3 min) followed by a final 5 min step at 72° C. Primers (at 40 uM concentration each), a specified amount of template, and 2.5 units of Taq polymerase (Perkin Elmer Cetus) were used in a final volume of 50 ul with the reaction buffer as recommended by the manufacturer.

Three primary PCR reactions were initially carried out, with 10 ng of template per reaction, using the primer pairs $A_L$ with $B_L$, $C_L$ with $D_L$, $E_L$ with $F_L$ respectively. The products of these PCR reactions, fragments $AB_L$, $CD_L$ and $EFL$ respectively, were purified using Qiaquick PCR Purification Kit (Qiagen Ltd, Surrey, UK, product #28104) following the protocol recommended by the manufacturer. Fragments $AB_L$ and $C_{DL}$ were combined using one tenth of each purified product, and subjected to recombinant PCR reactions with primers $A_L$ and $D_L$. The product of this reaction, fragment $AD_L$ was purified as above, and one tenth of the product was combined in a recombinant PCR reaction with one tenth of purified $EF_L$ using primers $A_L$ and $F_L$. The final humanised light chain recombinant PCR product, $AF_L$, and 94 the mouse amino acid was retained. At all other positions the human amino acid was used for the humanised heavy chain framework.

A file of the humanised heavy chain variable sequence was generated and a GCG program was used to identify silent sites for the following enzymes: EagI; NheI; XbaI; XhoI; XmaI.

Changes in the nucleotide sequence were made to include these restriction enzyme sites without changing the amino acid sequence. The presence of these sites were included to make cutting and pasting fragments of PCR clones easier.

A HindIII restriction site for cloning, a Kozac sequence for transcription initiation, and a murine signal sequence (MAWVWTLLFLMAAAQSAQA—SEQ ID 16) for protein secretion were added to the 5' end of the humanised heavy chain variable region sequence. An SpeI restriction site was added to the 3' end for cloning.

The humanised variable heavy chain framework with mouse CDRs was built by PCR using long overlapping oligonucleotides. Eight oligos were synthesised approximately 60 base pairs with 15 base pair overlaps. The oligos were as follows:

```
AH:SEQ ID NO 29. 5' ACA CgA AgC TTC ACC ATg gCT Tgg gTg Tgg ACC
                 TTg CTA TTC CTg ATg gCg gCC gCC CAA 3'
BH:SEQ ID NO 30: 5' CTT TAC CAA gCC TCC CCC AgA CTC CAC CAg
                 CTg CAC CTC TgC TTg ggC ACT TTg ggC ggC CgC CAT 3'
```

```
                                -continued
CH:SEQ ID NO 31: 5' TTg gTA AAg CCC ggg ggg TCC CTT AgA CTC TCC
                    TgT gCA gCT AgC ggA TTC ACT TTC AgT 3'
DH:SEQ ID NO 32: 5' CCC CTT CCC Tgg AgC CTg gCg gAC CCA ggA CAT
                    CCA gTA gCC ACT gAA AgT gAA TCC gCT 3'
EH:SEQ ID NO 33: 5' ggg AAg ggg CTc gAg Tgg gTT gCT gAA ATT AgA
                    TTg AAA TCT gAT AAT TAT gCA ACA CAT 3'
FH:SEQ ID NO 34: 5' ATC ATC TCT TgA gAT ggT gAA TTT CCC CTT CAC
                    AgA CTC CgC ATA ATg TgT TgC ATA ATT 3'
GH:SEQ ID NO 35: 5' ATC TCA AgA gAT gAT TCA AAA TCT AgA CTg TAT
                    CTg CAA ATg AAC AgC CTg AAA ACC gAg gAC ACA 3'
HH:SEQ ID NO 36: 5' ggT gAC TAg TgT TCC CTg gCC CCA gTC TAT gAA
                    ATC TgT ACA gTA ATA CAC ggC TgT gTC CTC ggT TTT 3'
```

The murine CDR's were grafted on to the template using recombinant PCR. PCR was performed using a programmable thermal cycler (Trio; Biometra). A 50 µl reaction contained 2.5 units of AmpliTaq polymerase (Perkin-Elmer-Cetus, Beaconsfield, UK) in the buffer supplied by the manufacturer, a buffer which provides the preferred pH and ionic strength for amplification (10 mM Tris-HCl, pH 8.3, 50 mM KCl and 1.5 mM MgCl$_2$), 200 µM each of dATP, dCTP, dGTP, and dTTP, and amplification primers at 1 µg/µl. The samples were heated to 94° C. for 2 minutes in a heating block, then centrifuged for 30 seconds at 16,000×G. Samples were placed on ice for 1 minute, then Taq polymerase and a drop of mineral oil added to each sample. The samples were vortexed, then centrifuged for 30 seconds at 16,000×G. Samples were placed in the thermal cycler programmed as follows:

Step 1: 94° C. for 1 minute
Step 2: 50° C. for 2 minutes, ramping up to step 3 at 0.4° C./second
Step 3: 72° C. for 3 minutes, go to step 1 repeating the loop 25 times Seven primary PCR reactions were initially performed with 1 µg/µl of each primer per reaction, using the primer combinations $A_H$ and $B_H$, $C_H$ and $D_H$, $E_H$ and $F_H$, $G_H$ and $H_H$; $A_H B_H C_H$ and $D_H E_H F_H G_H$ and $_H$; $A_H$; $B_H C_H D_H E_H F_H G_H$ and $H_H$. A 1 ul aliquot of the primary PCR reaction products were combined with primers (1 ug/ul) and subjected to the same PCR reaction conditions described for the primary PCR reactions to generate the full length heavy chain variable region. Primary PCR reaction fragments $AF_H$ and $EH_H$ fragment, $AH_H$, fragments $AB_H$, $GH_H$, and $AH_H$, fragments $AB_H$, $CD_H$, $EF_H$, and $GH_H$, fragments $AB_H$, $CD_H$, $EF_H$, $GH_H$, and $AH_H$ were combined with primers $A_H$ and $H_H$. All of the PCR reactions produced full length fragments. The humanised heavy chain variable region PCR product from the $AB_H$, $GH_H$, and $AH_H$ reaction was purified using Wizard PCR Preps DNA Purification System (Promega) following the protocol recommended by the manufacturer. The purified products were cut with Hind III and Spe I then cloned into a pUC vector containing a mutated IgG1 constant region (see below).

Construction of the Humanised Antibody

The humanised heavy chain variable region PCR products were cut with Hind III and Spe I then cloned into a pUC vector containing a mutated IgG1 constant region (see below). The variable region of the clones were sequenced FIGS. 3 and 4(SEQ IDS 17 and 18). A clone containing the correct humanised heavy chain variable amino acid sequence was selected. This clone had one silent nucleotide change from the model humanised heavy chain variable sequence.

An IgG1 with mutations to eliminate C1q and Fc binding was used for the constant region of the humanised heavy chain. These mutations were based on the following two papers: Duncan, A. R. and Winter, G. Localization of the C1q binding site on antibodies by surface scanning. Nature 332, 738–740, 1988 and Duncan, A. R., Woolf, J. M., Partridge, L. J., Burton, D. R. and Winter, G. Localisation of the binding site for human FcR1 on IgG. Nature 332, 563–564, 1988.

The residues mutated are shown in Kabat, E. A., Wu, T. T., Perry, H. M., Gottesman, K. S. and C. Foeller, 1991, Sequences of Proteins of Immunological Interest, Volume 1, page 680.

The changes made in IgG1 to create an IgG1 isotype lacking cytotoxicity were as follows: 248 Leu (CTg) to Ala (gCg) and 250 Gly (ggA) to Ala (gCA).

These mutations were made by site directed mutagenesis of a human IgG1 as follows:

Constant region PCR oligos used to generate IgG1 with mutations were:

```
SEQID 37 A_c  gCT gCT CCT TTT AAg CTT Tgg ggT CAA ggC TCA CTA gTC
              ACA gTC TCC
SEQID 38 B_c  TgA Cgg TgC CCC CgC gAg TTC Agg
SEQID 39 C_c  CCT gAA CTC gCg ggg gCA CCg TCA
SEQID 40 D_c  AAg CTT CCg TCg AAT TCA TTT ACC Cgg AgA CAg
```

Oligo $A_c$ contains a Hind/SpeI site. Oligos $B_c$ and $C_c$ contain the mutations at positions 248 and 250. Oligo $D_c$ contains an Eco R1 site. Oligos $A_c$ and $B_c$ were used to generate a fragment AB using the PCR conditions specified in the General Methodology section of this application and a cloned human IgG1 constant region as template (Reichmann, L., Clark, M., Waldmann, H., and Winter, G. (1988) Reshaping human antibodies for therapy, Nature 322, 323–327). Oligos Cc and Dc were used to generate fragment CD using the same PCR conditions and template as for AB. PCR fragments AB and CD were cleansed using a Wizard PCR Preps DNA Purification System (Promega). PCR fragments AB (5.0 ul) and $CD_c$ (5.0 ul) were combined with oligos $A_c$ and $D_c$ to generate a fragment $AD_c$ containing the IgG1 constant region with mutations. Fragment $AD_c$ was cleaned by Wizard PCR Preps DNA Purification System (Promega), digested with HindIII and Eco R1, then ligated into HindIII-EcoR 1 digested pEE6 plasmid containing the humanised anti-CD23 heavy chain variable region.

The constant region was sequenced to confirm the mutations. A fragment containing these mutations was transferred to an expression plasmid pEE6 containing the humanised anti-CD23 heavy chain variable region.

The humanised light chain variable region PCR products were cut with Hind III and BsiW 1, then cloned into expression plasmid pEE12 containing the human kappa light chain constant region described above. The clones were sequenced using an ABI fluorescent sequencer and a clone containing the correct amino acid sequence for humanised light chain variable region was selected.

A Bgl II—Sal I fragment containing the humanised heavy chain anti-CD23 from the pEE6 plasmid was ligated into the Bam H1—Sal I site of the pEE12 plasmid containing the humanised light chain anti-CD23 to make one plasmid containing both the humanised heavy and light chain anti-CD23. The humanised heavy chain variable and constant region and the humanised light chain variable and constant region in the final expression plasmid were sequenced.

Transient Expression of Humanised Antibody

The plasmid with the humanised anti-CD23 was transfected into COS cells and transiently expressed using the same protocol as described for the chimaeric antibody above. The expression plasmid with the humanised anti-CD23 was transfected into COS cells and transiently expressed as described for the chimeric anti-CD23 transient expression.

The concentration of chimeric and humanised anti-CD23 antibody required for half-maximal binding to sCD23 was assayed using the sCD23 ELISA already described. Absorbance at 405 nm was plotted versus a range of concentrations of antibody to generate a sigmoidal curve with a "goodness of fit" or correlation coefficient of 1. The absorbance was read using a Molecular Devices plate reader (Menlo Park, Calif., USA) and Softmax (Molecular Devices Corp) software to calculate best fit by a log-logit algorithm then display the curve, equation parameters and correlation coefficient. A discussion of curve fitting appears in "Data Analysis and Quality Control of Assays: A Practical Primer", by R P Channing Rogers in Practical Immuno Assay, editor Wilfrid R Butt; published by Marcel Dekker, Inc., New York 1984. The curve fitting algorithm for the log-logit logistic equations were based on the Levenberg-Marquardt Method. Discussion of this method can be found in Numerical Principles in C: The Art of Science computing by William H Press, Brian P Flannery, Saul A Teukolski and William T Vetterling, published by Cambridge University Press, New York, 1988. The value for x in ng/ml was calculated for the following equation:

$$x = cx\frac{[a-y]}{[y-d]}1/b$$

$$\text{when } y + \frac{d-c}{2}$$

and where d is the y-value corresponding to the asymptote at high values of the x-axis a is the y-value corresponding to the asymptote at low values of the x-axis c is the x-value corresponding to the midpoint between a and d b describes how rapidly the curve makes its transition from the asymptotes in the center of the curve, typically 1.

Figure 6:
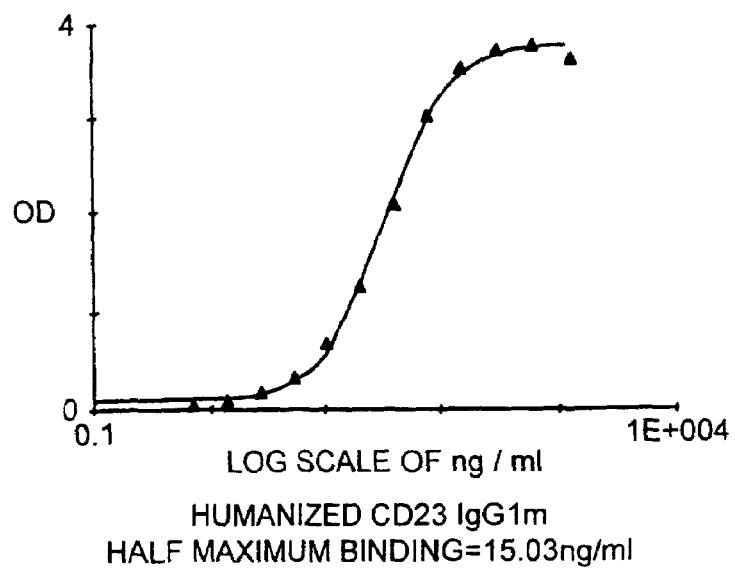
FIG. 6 shows the half maximal binding of humanised CD23 IgG1 m

The half-maximal binding of sCD23 by chimaeric anti-CD23 was 16.28 ng/ml (See FIG. 5). The half-maximal binding constant for the humanised anti-CD23 was 15.03 ng/ml (see FIG. 6) This data shows that the humanised anti-CD23 has equivalent binding to the chimaeric anti-CD23 which has a complete mouse C11 variable region.

Stable Expression

Stable cell lines expressing humanised anti-CD23 were selected using the glutaminine synthetase gene amplification system obtained from Celltech. The basic system described in Bebbington et al, 1992, Biotechnology 10, 169–175 was followed. This system describes making stable cell lines by introducing linearized expression vectors containing the cDNA encoding hamster glutamine synthetase under the control of the SV40 Early promoter and SV40 splicing and polyadenylation signal and the cDNA for the antibody heavy and light chain into mammalian cells by electroporation. Transfected cells are then selected for the ability to grow in glutamine free medium. NSO cells (non-immunoglobulin secreting mouse myeloma B cells) used for making the humanised anti-CD23 stable cell lines were grown in Iscove's Modified Dulbecco's Medium (Sigma) with 2 mM glutamine (GIBCO/BRL) and 10% fetal calf serum (Hyclone) (Non-Select media). The anti-CD23 cell lines were made as follows. The expression plasmid containing the humanised anti-CD23 (40 ug) was linearised with FsP1 (New England Biolabs), ethanol precipitated and resuspended in 50 $\mu$l of sterile water. Exponentially growing NSO cell were counted. The cells ($10^7$) were centrifuged and washed once in phosphate bufferd saline (PBS). The cells were resuspended in 950 $\mu$l of sterile PBS. The DNA, then cells, were added to an electroporation cuvette (0.4 mm, Bio-Rad) on ice. The cuvette was placed in a Bio-Rad electroporator and two consecutive pulses at 1500 volts, 3 $\mu$F were delivered. The cuvette was removed and placed on ice. The cells were diluted to $10^4$, $10^3$, $10^2$ cells/ml in Non-select media and plated in 96 well plates (Costar), 50 $\mu$l/well. The next day 150 $\mu$l of Iscove's Dulbecco's Modified Medium (Sigma) with 60 $\mu$g/ml glutamic acid (Sigma), 60 $\mu$g/ml asparagine (Sigma), 7 $\mu$g/ml each of adenosine (Sigma), guanosine (Sigma), cytidine (Sigma), uridine (Sigma), and thymidine (Sigma), and 10% fetal calf serum (Hyclone) (Select media) was added to each well. The plates were returned to a 37° C. incubator and left until substantial cell death had occurred and discrete surviving colonies appeared.

Colonies were transferred from a confluent 96 well plate to one well of a 24 well plate, then after several days, the confluent well from the 24 well plate was used to innoculate a 25 cm$^2$ flask. The spent media was included with fresh Select media to perform each expansion. Once in flasks, the cultures were maintained at between $10^5$ and $10^6$ cells/ml. The specific production rate (SPR) of 144 clones was performed to compare antibody production in each clone so that the highest producing clone could be selected as a production line. The SPR was performed by taking $10^6$ cells from a confluent flask, washing the cells with PBS, then adding the cells to 10 ml of fresh media for 24 hours at 37° C. The antibody production was quantitated by ELISA.

The clones were first screened for production of human IgG using an ELISA assay as follows. EIA/RIA plates (Costar) were coated with 100 $\mu$l/well of 5 $\mu$g/ml goat anti-human IgG (Jackson Immunoresearch Labs #109-001-003) in 35 mM NaHCO$_3$, 15 mM Na$_2$CO$_3$, pH 9.3 overnight at 4° C. Plates were washed three times with 150 mM NaCl, 50 mM Trizma base, 0.1% (v/v) Tween-20, pH 7.4 (TBS/

Tween), blocked for 1–2 hours at 22° C. with 100 μl/well of 2% bovine serum albumin in TBS/Tween, and washed three times with TBS/Tween. One hundred microliters of control Campath-1H IgG1 [Page, M J and Sydenham (1991) (supra)] standard (1000 ng/ml–1 ng/ml) in control media or sample supernatants were added, in triplicate, to wells and incubated overnight at 4° C. Plates were washed five times with TBS/Tween and 100 μl of a 1:5000 dilution of goat anti-human alkaline phosphatase conjugate (Jackson Immunoresearch Labs #109-055-088) was added and incubated for 2 hours at 22° C. or overnight at 4° C. The plates were washed five times with TBS/Tween and 100 μl of 3 mM pNPP in substrate buffer (Sigma 104-0) was added and the plates read at 405 nm on a microtiter plate reader (Molecular Devices) using a 20 minute kinetic program. Standard curves and sample IgG concentrations were calculated and reported directly by the program. The SPR was expressed as $\mu g/10^6$ cells/24 hours. The SPRs of the 144 clones ranged from 14–0 $\mu g/10^6$ cells/24 hours. Clones expressing at least 5 $\mu g/10^6$ cells/24 hours were also tested for binding to sCD23 using the ELISA assay already described. Chimaeric CD23 was used as the standard for these assays.

Complement Lysis and ADCC Assays

FITC labelled humanised anti-CD23 was used to confirm expression of surface CD23 on RPMI 8866 cells by flow cytometry. The same cell were stained with FITC labelled humanised anti-CDw52 antibody (hCD52) and found to be negative for $CD_{52}$ expression. In contrast, Wein 133 cells stained positive for hCD52 but negative for anti-CD23.

RPMI 8866 cells were stained with europium diethylene triaminopentaaccetate (Eu/DTPA) whilst Wein 133 cells were labelled with samarium diethylene triaminopentaacetate (Sm/DTPA) according to the methods described (Blomberg, K, 1993, J. Immunol. Methods. 168,267; Patel et al, 1995. J. Immunol. Methods. 184,29). A1:1 mixture of labelled Wein 133 cells and RPMI 8866 cells were then lysed with either hCD52 or anti-CD23 in the presence of NHS as a source of complement. Activation of complement through the classical pathway by hCD52 caused a release of Sm/DTPA. No Sm/DTPA was released in the presence of anti-CD23. The data confirms that only hCD52 and not anti-CD23 induces lysis of Wein 133 cells. The data further confirms that the complement pathway can be activated to cause cell lysis. No Eu/DTPA from RPMI 8866 was released by hCD52 as anticipated. Although RPMI 8866 cells express CD23, no Eu/DTPA was release by anti-CD23, demonstrating that the antibody is unable to activate complement.

Lysis of 1:1 mixture labelled Wein 133 and RPMI 8866 by antibody dependent cellular cytoxicity (ADCC) was attempted with either anti-CD23 or hCD52 in the presence of peripheral blood mononoclear cells (PBMC). A release of Sm/DTPA by hCD52 and not anti-CD23 confirmed that only the latter was unable to mediate ADCC lysis of Wein 133 cells. This was not surprising, since Wein 133 cells do not express CD23. Neither of the antibodies caused a release of Eu/DTPA. This suggested that although CD23 expression was confirmed on RPMI 8866 cells by flow cytometry, no ADCC mediated cell lysis was detected with anti-CD23.

Kinetic Analysis

The association rate, dissociation rate and the dissociation rate constant for the binding of humanised anti-CD23 to the CD23 antigen was evaluated on the Biacore Biosensor. Briefly, purified recombinant CD23 was immobilised onto a CM5 sensor surface. Carboxyl groups on the dextran surface were activated by 1-ethyl-3(3-dimethylaminopropyl) carbidimide (EDCO/N-hydroxysuccimimide (NHS). Following activation, recombinant CD23 was passed over the surface to initiate immobilisation. Ethanolamine was then added to quench residual active groups. Humanised anti-CD23 diluted in HBS buffer was passed over the sensor surface. Binding of anti-CD23 to immobilised CD23 was monitored in real time for estimation of the association rate ($M^{-1}$ $seq^{-1}$). Dissociation of the CD23 and the anti-CD23 complex in buffer was also monitored for estimation of the dissociation rate ($sec^{-1}$). The dissociation constant (nM) was calculated from the dissociation and association rate. For 6 batches of anti-CD23, the data shows association rates in the range $1.5-1.85 \times 10^6$ $M^{-1}$ $sec^{-1}$ and the dissociation rate of $1-2 \times 10^5$ $sec^{-1}$. The dissociation constant for anti-CD23 was found to be within 8–12 pM. The affinity constant was determined to be approximately $9 \times 10^{10}$ Ka $mol^{-1}$.

What is claimed is:

1. An isolated diagnostic monoclonal antibody binds specifically to the CD23 (FCRεII) type II molecule expressed on haematopoietic cells, said monoclonal antibody comprising light chain variable domains CDRL1, CDRL2, and CDRL3, further comprising heavy chain variable domains CDRH1, CDRH2, and CDRH3, wherein CDRL1 consists of the amino acid sequence RSSKSLLY KDGKTYLN of SEQ ID NO:1, CDRL2 consists of the amino acid sequence LMSTRAS of SEQ ID NO:5, CDRL3 consists of the amino acid sequence QQLVEYPFT of SEQ ID NO:7, CDRH1 consists of the amino acid sequence GYWMS of SEQ ID NO:9, CDRH2 consists of amino acid sequence EIRLKSDNYATHYAESVKG of SEQ ID NO:11, and CDHR3 consists of amino acid sequence FID of SEQ ID NO:13.

2. The isolated diagnostic monoclonal antibody according to claim 1 which binds to CD23 with an affinity constant equal to or greater than $1 \times 10^9$ Ka Mol$^{-1}$.

3. The isolated diagnostic monoclonal antibody according to claim 1, wherein said antibody is a chimeric antibody.

4. The isolated diagnostic monoclonal antibody according to claim 1, wherein said antibody is a humanised antibody.

5. The isolated diagnostic monoclonal antibody according to claim 1, wherein the framework of the heavy chain retains the mouse heavy chain amino acid residues at positions 49, 66, 76, 77 and 94 according to FIG. 1 (SEQ ID NO:1), and the framework of the light chain retains the mouse light chain amino acid residue at position 64 according to FIG. 2 (SEQ ID NO:2).

6. An isolated diagnostic antibody that binds to the CD23 (FCRεII) type II molecule expressed on haematopoietic cells comprising both of the amino acid sequences encoded by the nucleotide sequences according to SEQ ID NO:1 and SEQ ID NO:2.

7. An isolated diagnostic antibody that binds to the CD23 (FCRεII) type II molecule expressed on haematopoietic cells comprising both of the amino acid sequences encoded by the nucleotide sequences according to SEQ ID NO:17 and SEQ ID NO:18.

8. A pharmaceutical formulation comprising the diagnostic monoclonal antibody as defined in claim 1 and a pharmaceutically acceptable excipient.

9. A pharmaceutical formulation comprising the diagnostic monoclonal antibody as defined in claim 1 in combination with an anti-inflammatory agent and a pharmaceutically acceptable excipient.

10. A method of treatment of rheumatoid arthritis in a patient in need thereof, said method comprising the step of administering to the patient a pharmaceutically effective amount of the monoclonal antibody according to claim 1.

* * * * *

SEQUENCE LISTING

<160> NUMBER OF SEQ ID NOS: 54

<210> SEQ ID NO 1
<211> LENGTH: 415
<212> TYPE: DNA
<213> ORGANISM: Mus musculus
<220> FEATURE:
<221> NAME/KEY: CDS
<222> LOCATION: (3)..(413)

<400> SEQUENCE: 1

```
aa gct tta cag tta ctc agc aca cag gac ctc acc atg gat ttt ggg        47
   Ala Leu Gln Leu Leu Ser Thr Gln Asp Leu Thr Met Asp Phe Gly
    1               5                  10                  15 ctg att ttt ttt att gtt ctt tta aaa ggg gtc cag agt gaa gtg aag    95
Leu Ile Phe Phe Ile Val Leu Leu Lys Gly Val Gln Ser Glu Val Lys
                20                  25                  30 ctt gag gag tct gga gga ggc ttg gtg caa cct gga gga tcc atg aaa   143
Leu Glu Glu Ser Gly Gly Gly Leu Val Gln Pro Gly Gly Ser Met Lys
            35                  40                  45
```

```
ctc tcc tgt gta gcc tct gga ttt act ttc agt ggc tac tgg atg tct      191
Leu Ser Cys Val Ala Ser Gly Phe Thr Phe Ser Gly Tyr Trp Met Ser
         50                  55                  60 tgg gtc cgc cag tct cca gag aag ggg ctt gag tgg gtt gct gaa att      239
Trp Val Arg Gln Ser Pro Glu Lys Gly Leu Glu Trp Val Ala Glu Ile
 65                  70                  75 aga ttg aaa tct gat aat tat gca aca cat tat gcg gag tct gtg aaa      287
Arg Leu Lys Ser Asp Asn Tyr Ala Thr His Tyr Ala Glu Ser Val Lys
 80                  85                  90                  95 ggg aag ttc acc atc tca aga gat gat tcc aaa agt cgt ctc tac ctg      335
Gly Lys Phe Thr Ile Ser Arg Asp Asp Ser Lys Ser Arg Leu Tyr Leu
                100                 105                 110 caa atg aac agc tta aga gct gaa gac agt gga gtt tat tac tgt aca      383
Gln Met Asn Ser Leu Arg Ala Glu Asp Ser Gly Val Tyr Tyr Cys Thr
            115                 120                 125 gat ttc ata gac tgg ggc caa ggg aca cta gt                            415
Asp Phe Ile Asp Trp Gly Gln Gly Thr Leu
        130                 135

<210> SEQ ID NO 2
<211> LENGTH: 437
<212> TYPE: DNA
<213> ORGANISM: Mus musculus
<220> FEATURE:
<221> NAME/KEY: CDS
<222> LOCATION: (3)..(437)

<400> SEQUENCE: 2 aa gct tta cag tta ctc agc aca cag gac ctc acc atg agg ttc tct       47
   Ala Leu Gln Leu Leu Ser Thr Gln Asp Leu Thr Met Arg Phe Ser
    1               5                  10                  15 gtt cag ttt ctg ggg gtg ctt atg ttc tgg atc tct gga gtc agt ggg       95
Val Gln Phe Leu Gly Val Leu Met Phe Trp Ile Ser Gly Val Ser Gly
             20                  25                  30 gat att gtg ata acc cag gat gaa ctc tcc aat cct gtc act tct gga      143
Asp Ile Val Ile Thr Gln Asp Glu Leu Ser Asn Pro Val Thr Ser Gly
         35                  40                  45 gaa tca gtt tcc atc tcc tgc agg tct agt aag agt ctc ctg tat aag      191
Glu Ser Val Ser Ile Ser Cys Arg Ser Ser Lys Ser Leu Leu Tyr Lys
 50                  55                  60 gat ggg aag aca tac ttg aat tgg ttt ctg cag aga cca gga caa tct      239
Asp Gly Lys Thr Tyr Leu Asn Trp Phe Leu Gln Arg Pro Gly Gln Ser
 65                  70                  75 cct cag ctc ctg atg tat ttg atg tcc acc cgt gca tca gga gtc tca      287
Pro Gln Leu Leu Met Tyr Leu Met Ser Thr Arg Ala Ser Gly Val Ser
 80                  85                  90                  95 gac cgg ttt agt ggc agt ggg tca ggc aca gat ttc acc ctg gaa atc      335
Asp Arg Phe Ser Gly Ser Gly Ser Gly Thr Asp Phe Thr Leu Glu Ile
                100                 105                 110 agt aga gtg aag gct gag gat gtg ggt gtg tat tac tgt caa caa ctt      383
Ser Arg Val Lys Ala Glu Asp Val Gly Val Tyr Tyr Cys Gln Gln Leu
            115                 120                 125 gta gag tat cca ttc acg ttc ggc tcg ggg aca aag ttg gaa ata aaa      431
Val Glu Tyr Pro Phe Thr Phe Gly Ser Gly Thr Lys Leu Glu Ile Lys
        130                 135                 140 cgt acg                                                              437
Arg Thr
    145

<210> SEQ ID NO 3
<211> LENGTH: 16
```

```
<212> TYPE: PRT
<213> ORGANISM: Mus musculus

<400> SEQUENCE: 3

Arg Ser Ser Lys Ser Leu Leu Tyr Lys Asp Gly Lys Thr Tyr Leu Asn
 1               5                  10                  15

<210> SEQ ID NO 4
<211> LENGTH: 48
<212> TYPE: DNA
<213> ORGANISM: Mus musculus
<220> FEATURE:
<221> NAME/KEY: CDS
<222> LOCATION: (1)..(48)

<400> SEQUENCE: 4 cgc tcg agt aag agt ctc ctg tat aag gat ggg aag aca tac ttg aat      48
Arg Ser Ser Lys Ser Leu Leu Tyr Lys Asp Gly Lys Thr Tyr Leu Asn
 1               5                  10                  15

<210> SEQ ID NO 5
<211> LENGTH: 7
<212> TYPE: PRT
<213> ORGANISM: Mus musculus

<400> SEQUENCE: 5

Leu Met Ser Thr Arg Ala Ser
 1               5

<210> SEQ ID NO 6
<211> LENGTH: 21
<212> TYPE: DNA
<213> ORGANISM: Mus musculus
<220> FEATURE:
<221> NAME/KEY: CDS
<222> LOCATION: (1)..(21)

<400> SEQUENCE: 6 ttg atg tcc acc cgg gca tca                                          21
Leu Met Ser Thr Arg Ala Ser
 1               5

<210> SEQ ID NO 7
<211> LENGTH: 9
<212> TYPE: PRT
<213> ORGANISM: Mus musculus

<400> SEQUENCE: 7

Gln Gln Leu Val Glu Tyr Pro Phe Thr
 1               5

<210> SEQ ID NO 8
<211> LENGTH: 27
<212> TYPE: DNA
<213> ORGANISM: Mus musculus
<220> FEATURE:
<221> NAME/KEY: CDS
<222> LOCATION: (1)..(27)

<400> SEQUENCE: 8 caa cag ctg gta gag tat cca ttc acg                                  27
Gln Gln Leu Val Glu Tyr Pro Phe Thr
 1               5

<210> SEQ ID NO 9
<211> LENGTH: 5
<212> TYPE: PRT
```

<213> ORGANISM: Mus musculus

<400> SEQUENCE: 9

Gly Tyr Trp Met Ser
 1               5

<210> SEQ ID NO 10
<211> LENGTH: 15
<212> TYPE: DNA
<213> ORGANISM: Mus musculus
<220> FEATURE:
<221> NAME/KEY: CDS
<222> LOCATION: (1)..(15)

<400> SEQUENCE: 10 ggc tac tgg atg tcc                                              15
Gly Tyr Trp Met Ser
 1               5

<210> SEQ ID NO 11
<211> LENGTH: 19
<212> TYPE: PRT
<213> ORGANISM: Mus musculus

<400> SEQUENCE: 11

Glu Ile Arg Leu Lys Ser Asp Asn Tyr Ala Thr His Tyr Ala Glu Ser
 1               5                  10                  15

Val Lys Gly

<210> SEQ ID NO 12
<211> LENGTH: 57
<212> TYPE: DNA
<213> ORGANISM: Mus musculus
<220> FEATURE:
<221> NAME/KEY: CDS
<222> LOCATION: (1)..(57)

<400> SEQUENCE: 12 gaa att aga ttg aaa tct gat aat tat gca aca cat tat gcg gag tct      48
Glu Ile Arg Leu Lys Ser Asp Asn Tyr Ala Thr His Tyr Ala Glu Ser
 1               5                  10                  15 gtg aag ggg                                                      57
Val Lys Gly

<210> SEQ ID NO 13
<211> LENGTH: 3
<212> TYPE: PRT
<213> ORGANISM: Mus musculus

<400> SEQUENCE: 13

Phe Ile Asp
 1

<210> SEQ ID NO 14
<211> LENGTH: 9
<212> TYPE: DNA
<213> ORGANISM: Mus musculus
<220> FEATURE:
<221> NAME/KEY: CDS
<222> LOCATION: (1)..(9)

<400> SEQUENCE: 14 ttc ata gac                                                       9
Phe Ile Asp
 1

<210> SEQ ID NO 15
<211> LENGTH: 19
<212> TYPE: PRT
<213> ORGANISM: Artificial Sequence
<220> FEATURE:
<223> OTHER INFORMATION: Description of Artificial Sequence: Synthetic
      sequence

<400> SEQUENCE: 15

Met Gly Trp Ser Cys Ile Ile Leu Phe Leu Val Ala Thr Ala Thr Gly
 1               5                  10                  15

Val His Ser

<210> SEQ ID NO 16
<211> LENGTH: 19
<212> TYPE: PRT
<213> ORGANISM: Artificial Sequence
<220> FEATURE:
<223> OTHER INFORMATION: Description of Artificial Sequence: Synthetic
      sequence

<400> SEQUENCE: 16

Met Ala Trp Val Trp Thr Leu Leu Phe Leu Met Ala Ala Ala Gln Ser
 1               5                  10                  15

Ala Gln Ala

<210> SEQ ID NO 17
<211> LENGTH: 348
<212> TYPE: DNA
<213> ORGANISM: Artificial Sequence
<220> FEATURE:
<223> OTHER INFORMATION: Description of Artificial Sequence: Humanised
      anti-CD23 antibody VL region
<220> FEATURE:
<221> NAME/KEY: CDS
<222> LOCATION: (1)..(348)

<400> SEQUENCE: 17

```
gat att gtg atg act cag tct cca ctc tcc ctg ccc gtc acc cct gga      48
Asp Ile Val Met Thr Gln Ser Pro Leu Ser Leu Pro Val Thr Pro Gly
 1               5                  10                  15 gag ccg gcc tcc atc tcc tgt cgc tcg agt aag agt ctc ctg tat aag      96
Glu Pro Ala Ser Ile Ser Cys Arg Ser Ser Lys Ser Leu Leu Tyr Lys
                20                  25                  30 gat ggg aag aca tac ttg aat tgg tac ctg cag aag cca ggg cag tct     144
Asp Gly Lys Thr Tyr Leu Asn Trp Tyr Leu Gln Lys Pro Gly Gln Ser
            35                  40                  45 cca cag ctc ctg atc tat ttg atg tcc acc cgg gca tca ggg gtc cct     192
Pro Gln Leu Leu Ile Tyr Leu Met Ser Thr Arg Ala Ser Gly Val Pro
        50                  55                  60 gac agg ttc agt ggc agt gga tca ggc aca gat ttt aca ctg aaa atc     240
Asp Arg Phe Ser Gly Ser Gly Ser Gly Thr Asp Phe Thr Leu Lys Ile
 65                  70                  75                  80 agc aga gtg gag gct gag gat gtt ggg gtt tat tac tgt caa cag ctg     288
Ser Arg Val Glu Ala Glu Asp Val Gly Val Tyr Tyr Cys Gln Gln Leu
                85                  90                  95 gta gag tat cca ttc acg ttc ggc caa ggg acc aag gtg gag atc aaa     336
Val Glu Tyr Pro Phe Thr Phe Gly Gln Gly Thr Lys Val Glu Ile Lys
                100                 105                 110 cgt acg gtg gct                                                     348
Arg Thr Val Ala
            115
```

<210> SEQ ID NO 18
<211> LENGTH: 1335
<212> TYPE: DNA
<213> ORGANISM: Artificial Sequence
<220> FEATURE:
<223> OTHER INFORMATION: Description of Artificial Sequence: Humanised anti-CD23 antibody VH region
<220> FEATURE:
<221> NAME/KEY: CDS
<222> LOCATION: (1)..(1335)

<400> SEQUENCE: 18

```
gag gtg cag ctg gtg gag tct ggg gga ggc ttg gta aag ccc ggg ggg        48
Glu Val Gln Leu Val Glu Ser Gly Gly Gly Leu Val Lys Pro Gly Gly
 1               5                  10                  15 tcc ctt aga ctc tcc tgt gca gct agc gga ttc act ttc agt ggc tac        96
Ser Leu Arg Leu Ser Cys Ala Ala Ser Gly Phe Thr Phe Ser Gly Tyr
            20                  25                  30 tgg atg tcc tgg gtc cgc cag gct cca ggg aag ggg ctc gag tgg gtt       144
Trp Met Ser Trp Val Arg Gln Ala Pro Gly Lys Gly Leu Glu Trp Val
        35                  40                  45 gct gaa att aga ttg aaa tct gat aat tat gca aca cat tat gcg gag       192
Ala Glu Ile Arg Leu Lys Ser Asp Asn Tyr Ala Thr His Tyr Ala Glu
    50                  55                  60 tct gtg aag ggg aaa ttc acc atc tca aga gat gat tca aaa tct aga       240
Ser Val Lys Gly Lys Phe Thr Ile Ser Arg Asp Asp Ser Lys Ser Arg
65                  70                  75                  80 ctg tat ctg caa atg aac agc ctg aaa acc gag gac aca gcc gtg tat       288
Leu Tyr Leu Gln Met Asn Ser Leu Lys Thr Glu Asp Thr Ala Val Tyr
                85                  90                  95 tac tgt aca gat ttc ata gac tgg ggc cag gga aca cta gtc acc gtc       336
Tyr Cys Thr Asp Phe Ile Asp Trp Gly Gln Gly Thr Leu Val Thr Val
            100                 105                 110 tcc tca gcc tcc acc aag ggc cca tcg gtc ttc ccc ctg gca ccc tcc       384
Ser Ser Ala Ser Thr Lys Gly Pro Ser Val Phe Pro Leu Ala Pro Ser
        115                 120                 125 tcc aag agc acc tct ggg ggc aca gcg gcc ctg ggc tgc ctg gtc aag       432
Ser Lys Ser Thr Ser Gly Gly Thr Ala Ala Leu Gly Cys Leu Val Lys
    130                 135                 140 gac tac ttc ccc gaa ccg gtg acg gtg tcg tgg aac tca ggc gcc ctg       480
Asp Tyr Phe Pro Glu Pro Val Thr Val Ser Trp Asn Ser Gly Ala Leu
145                 150                 155                 160 acc agc ggc gtg cac acc ttc ccg gct gtc cta cag tcc tca gga ctc       528
Thr Ser Gly Val His Thr Phe Pro Ala Val Leu Gln Ser Ser Gly Leu
                165                 170                 175 tac tcc ctc agc agc gtg gtg acc gtg ccc tcc agc agc ttg ggc acc       576
Tyr Ser Leu Ser Ser Val Val Thr Val Pro Ser Ser Ser Leu Gly Thr
            180                 185                 190 cag acc tac atc tgc aac gtg aat cac aag ccc agc aac acc aag gtg       624
Gln Thr Tyr Ile Cys Asn Val Asn His Lys Pro Ser Asn Thr Lys Val
        195                 200                 205 gac aag aaa gtg gag ccc aaa tct tgt gac aaa act cac aca tgc cca       672
Asp Lys Lys Val Glu Pro Lys Ser Cys Asp Lys Thr His Thr Cys Pro
    210                 215                 220 ccg tgc cca gca cct gaa ctc gcg ggg gca ccg tca gtc ttc ctc ttc       720
Pro Cys Pro Ala Pro Glu Leu Ala Gly Ala Pro Ser Val Phe Leu Phe
225                 230                 235                 240 ccc cca aaa ccc aag gac acc ctc atg atc tcc cgg acc cct gag gtc       768
Pro Pro Lys Pro Lys Asp Thr Leu Met Ile Ser Arg Thr Pro Glu Val
                245                 250                 255 aca tgc gtg gtg gtg gac gtg agc cac gaa gac cct gag gtc aag ttc       816
Thr Cys Val Val Val Asp Val Ser His Glu Asp Pro Glu Val Lys Phe
```

```
                260             265                  270
aac tgg tac gtg gac ggc gtg gag gtg cat aat gcc aag aca aag ccg     864
Asn Trp Tyr Val Asp Gly Val Glu Val His Asn Ala Lys Thr Lys Pro
        275                 280                 285 cgg gag gag cag tac aac agc acg tac cgt gtg gtc agc gtc ctc acc     912
Arg Glu Glu Gln Tyr Asn Ser Thr Tyr Arg Val Val Ser Val Leu Thr
    290                 295                 300 gtc ctg cac cag gac tgg ctg aat ggc aag gag tac aag tgc aag gtc     960
Val Leu His Gln Asp Trp Leu Asn Gly Lys Glu Tyr Lys Cys Lys Val
305                 310                 315                 320 tcc aac aaa gcc ctc cca gcc ccc atc gag aaa acc atc tcc aaa gcc    1008
Ser Asn Lys Ala Leu Pro Ala Pro Ile Glu Lys Thr Ile Ser Lys Ala
                325                 330                 335 aaa ggg cag ccc cga gaa cca cag gtg tac acc ctg ccc cca tcc cgg    1056
Lys Gly Gln Pro Arg Glu Pro Gln Val Tyr Thr Leu Pro Pro Ser Arg
            340                 345                 350 gat gag ctg acc aag aac cag gtc agc ctg acc tgc ctg gtc aaa ggc    1104
Asp Glu Leu Thr Lys Asn Gln Val Ser Leu Thr Cys Leu Val Lys Gly
        355                 360                 365 ttc tat ccc agc gac atc gcc gtg gag tgg gag agc aat ggg cag ccg    1152
Phe Tyr Pro Ser Asp Ile Ala Val Glu Trp Glu Ser Asn Gly Gln Pro
    370                 375                 380 gag aac aac tac aag acc acg cct ccc gtg ctg gac tcc gac ggc tcc    1200
Glu Asn Asn Tyr Lys Thr Thr Pro Pro Val Leu Asp Ser Asp Gly Ser
385                 390                 395                 400 ttc ttc ctc tac agc aag ctc acc gtg gac aag agc agg tgg cag cag    1248
Phe Phe Leu Tyr Ser Lys Leu Thr Val Asp Lys Ser Arg Trp Gln Gln
                405                 410                 415 ggg aac gtc ttc tca tgc tcc gtg atg cat gag gct ctg cac aac cac    1296
Gly Asn Val Phe Ser Cys Ser Val Met His Glu Ala Leu His Asn His
            420                 425                 430 tac acg cag aag agc ctc tcc ctg tct ccg ggt aaa tga                1335
Tyr Thr Gln Lys Ser Leu Ser Leu Ser Pro Gly Lys
        435                 440

<210> SEQ ID NO 19
<211> LENGTH: 57
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 19
gatgaagctt tacagttact cagcacacag gacctcacca tggattttgg gctgatt     57

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 20
gatggactag tgtcccttgg cccca                                        25

<210> SEQ ID NO 21
<211> LENGTH: 57
<212> TYPE: DNA
<213> ORGANISM: Artificial Sequence
<220> FEATURE:
<223> OTHER INFORMATION: Description of Artificial Sequence:
```

Oligonucleotide

<400> SEQUENCE: 21
gatgaagctt tacagttact cagcacacag gacctcacca tgaggttctc tgttcag        57

<210> SEQ ID NO 22
<211> LENGTH: 28
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 22
gatgcgtacg tytkatytcc avcttkgt        28

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 23
gatcaagctt ctctacagtt actgagcaca        30

<210> SEQ ID NO 24
<211> LENGTH: 63
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 24
aatcaagtat gtcttcccat ccttatacag gagactctta ctcgagcgac aggagatgga     60
ggc        63

<210> SEQ ID NO 25
<211> LENGTH: 63
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 25
cgctcgagta agagtctcct gtataaggat gggaagacat acttgaattg gtacctgcag     60
aag        63

<210> SEQ ID NO 26
<211> LENGTH: 36
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 26
tgatgcccgg gtggacatca aatagatcag gagctg        36

<210> SEQ ID NO 27
<211> LENGTH: 36
<212> TYPE: DNA

-continued

```
<213> ORGANISM: Artificial Sequence
<220> FEATURE:
<223> OTHER INFORMATION: Description of Artificial Sequence:
      Oligonucleotide

<400> SEQUENCE: 27
ttgatgtcca cccgggcatc agggtccct gacagg                                  36

<210> SEQ ID NO 28
<211> LENGTH: 84
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 28
agccacctga cgtttgatct ccaccttggt cccttggccg aacgtgaatg gatactctac       60
cagctgttga cagtaataaa cccc                                              84

<210> SEQ ID NO 29
<211> LENGTH: 60
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 29
acacgaagct tcaccatggc ttgggtgtgg accttgctat tcctgatggc ggccgcccaa       60

<210> SEQ ID NO 30
<211> LENGTH: 66
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 30
ctttaccaag cctcccccag actccaccag ctgcacctct gcttgggcac tttgggcggc       60
cgccat                                                                  66

<210> SEQ ID NO 31
<211> LENGTH: 60
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 31
ttggtaaagc ccgggggtc ccttagactc tcctgtgcag ctagcggatt cactttcagt       60

<210> SEQ ID NO 32
<211> LENGTH: 60
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 32
ccccttccct ggagcctggc ggacccagga catccagtag ccactgaaag tgaatccgct       60
```

<210> SEQ ID NO 33
<211> LENGTH: 60
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 33 gggaagggge tcgagtgggt tgctgaaatt agattgaaat ctgataatta tgcaacacat    60

<210> SEQ ID NO 34
<211> LENGTH: 60
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 34
atcatctctt gagatggtga atttcccctt cacagactcc gcataatgtg ttgcataatt    60

<210> SEQ ID NO 35
<211> LENGTH: 66
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 35
atctcaagag atgattcaaa atctagactg tatctgcaaa tgaacagcct gaaaaccgag    60
gacaca                                                               66

<210> SEQ ID NO 36
<211> LENGTH: 69
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 36
ggtgactagt gttccctggc cccagtctat gaaatctgta cagtaataca cggctgtgtc    60
ctcggtttt                                                            69

<210> SEQ ID NO 37
<211> LENGTH: 48
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 37
gctgctcctt ttaagctttg gggtcaaggc tcactagtca cagtctcc                 48

<210> SEQ ID NO 38
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 38

```
tgacggtgcc cccgcgagtt cagg                                              24
```

<210> SEQ ID NO 39
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 39

```
cctgaactcg cgggggcacc gtca                                              24
```

<210> SEQ ID NO 40
<211> LENGTH: 33
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 40

```
aagcttccgt cgaattcatt tacccggaga cag                                    33
```

<210> SEQ ID NO 41
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 41

```
actagtcgac atgaagtttc cttctcaact tctgctc                                37
```

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence: Synthetic
      sequence

<400> SEQUENCE: 42

Thr Lys Leu Glu Ile Lys Arg Thr
 1               5

<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence: Synthetic
      sequence

<400> SEQUENCE: 43

Thr Lys Val Glu Ile Lys Arg Thr
 1               5

<210> SEQ ID NO 44
<211> LENGTH: 8
<212> TYPE: PRT
<213> ORGANISM: Artificial Sequence
<220> FEATURE:
<223> OTHER INFORMATION: Description of Artificial Sequence: Synthetic
      sequence

<400> SEQUENCE: 44

Thr Lys Leu Glu Ile Arg Arg Thr
 1               5

<210> SEQ ID NO 45
<211> LENGTH: 8
<212> TYPE: PRT
<213> ORGANISM: Artificial Sequence
<220> FEATURE:
<223> OTHER INFORMATION: Description of Artificial Sequence: Synthetic
      sequence

<400> SEQUENCE: 45

Thr Lys Val Glu Ile Arg Arg Thr
 1               5

<210> SEQ ID NO 46
<211> LENGTH: 415
<212> TYPE: DNA
<213> ORGANISM: Mus musculus

<400> SEQUENCE: 46
actagtgtcc cttggcccca gtctatgaaa tctgtacagt aataaactcc actgtcttca      60
gctcttaagc tgttcatttg caggtagaga cgacttttgg aatcatctct tgagatggtg     120 aacttcccctt tcacagactc cgcataatgt gttgcataat tatcgagattt caatctaatt    180 tcagcaaccc actcaagccc cttctctgga gactggcgga cccaagacat ccagtagcca     240
ctgaaagtaa atccagaggc tacacaggag agtttcatgg atcctccagg ttgcaccaag     300
cctcctccag actcctcaag cttcacttca ctctggaccc cttttaaaag aacaataaaa     360
aaaatcagcc caaaatccat ggtgaggtcc tgtgtgctga gtaactgtaa agctt         415

<210> SEQ ID NO 47
<211> LENGTH: 437
<212> TYPE: DNA
<213> ORGANISM: Mus musculus

<400> SEQUENCE: 47
cgtacgtttt atttccaact ttgtccccga gccgaacgtg aatggatact ctacaagttg      60
ttgacagtaa tacacaccca catcctcagc cttcactcta ctgatttcca gggtgaaatc     120
tgtgcctgac ccactgccac taaaccggtc tgagactcct gatgcacggg tggacatcaa     180
atacatcagg agctgaggag attgtcctgg tctctgcaga aaccaattca agtatgtctt     240
cccatcctta tacaggagac tcttactaga cctgcaggag atggaaactg attctccaga     300
agtgacagga ttggagagtt catcctgggt tatcacaata tccccactga ctccagagat     360
ccagaacata agcaccccca gaaactgaac agagaacctc atggtgaggt cctgtgtgct     420
gagtaactgt aaagctt                                                   437

<210> SEQ ID NO 48
<211> LENGTH: 348
<212> TYPE: DNA
<213> ORGANISM: Artificial Sequence
<220> FEATURE:
<223> OTHER INFORMATION: Description of Artificial Sequence: Humanised
      anti-CD23 antibody VL region

<400> SEQUENCE: 48
agccaccgta cgtttgatct ccaccttggt cccttggccg aacgtgaatg gatactctac      60
cagctgttga cagtaataaa ccccaacatc ctcagcctcc actctgctga ttttcagtgt     120
aaaatctgtg cctgatccac tgccactgaa cctgtcaggg acccctgatg cccgggtgga    180

```
catcaaatag atcaggagct gtggagactg ccctggcttc tgcaggtacc aattcaagta      240
tgtcttccca tccttataca ggagactctt actcgagcga caggagatgg aggccggctc      300
tccaggggtg acgggcaggg agagtggaga ctgagtcatc acaatatc                   348
```

<210> SEQ ID NO 49
<211> LENGTH: 1335
<212> TYPE: DNA
<213> ORGANISM: Artificial Sequence
<220> FEATURE:
<223> OTHER INFORMATION: Description of Artificial Sequence: Humanised
      anti-CD23 antibody VH region

<400> SEQUENCE: 49

```
tcatttaccc ggagacaggg agaggctctt ctgcgtgtag tggttgtgca gagcctcatg       60
catcacggag catgagaaga cgttcccctg ctgccacctg ctcttgtcca cggtgagctt      120
gctgtagagg aagaaggagc cgtcggagtc cagcacggga ggcgtggtct tgtagttgtt      180
ctccggctgc ccattgctct cccactccac ggcgatgtcg ctgggataga agcctttgac      240
caggcaggtc aggctgacct ggttcttggt cagctcatcc cggatggggg cagggtgta      300 cacctgtggt tctcggggct gccctttggc tttggagatg gttttctcga tggggctgg      360 gagggctttg ttggagacct tgcacttgta ctccttgcca ttcagccagt cctggtgcag      420
gacggtgagg acgctgacca cacggtacgt gctgttgtac tgctcctccc gcggctttgt      480
cttggcatta tgcacctcca cgccgtccac gtaccagttg aacttgacct cagggtcttc      540
gtggctcacg tccaccacca cgcatgtgac ctcagggtc cgggagatca tgagggtgtc      600
cttgggtttt ggggggaaga ggaagactga cggtgccccc gcgagttcag gtgctgggca      660
cggtgggcat gtgtgagttt tgtcacaaga tttgggctcc actttcttgt ccaccttggt      720
gttgctgggc ttgtgattca cgttgcagat gtaggtctgg gtgcccaagc tgctggaggg      780
cacggtcacc acgctgctga gggagtagag tcctgaggac tgtaggacag ccgggaaggt      840
gtgcacgccg ctggtcaggg cgcctgagtt ccacgacacc gtcaccggtt cggggaagta      900
gtccttgacc aggcagccca gggccgctgt gcccccagag gtgctcttgg aggagggtgc      960 caggggaag accgatgggc ccttggtgga ggctgaggag acggtgacta gtgttccctg     1020
gccccagtct atgaaatctg tacagtaata cacggctgtg tcctcggttt tcaggctgtt    1080
catttgcaga tacagtctag attttgaatc atctcttgag atggtgaatt tccccttcac    1140
agactccgca taatgtgttg cataattatc agatttcaat ctaatttcag caacccactc    1200 gagcccttc cctggagcct ggcggaccca ggacatccag tagccactga aagtgaatcc     1260
gctagctgca caggagagtc taagggaccc cccgggcttt accaagcctc ccccagactc    1320
caccagctgc acctc                                                    1335
```

<210> SEQ ID NO 50
<211> LENGTH: 137
<212> TYPE: PRT
<213> ORGANISM: Mus musculus

<400> SEQUENCE: 50

```
Ala Leu Gln Leu Leu Ser Thr Gln Asp Leu Thr Met Asp Phe Gly Leu
  1               5                  10                  15

Ile Phe Phe Ile Val Leu Leu Lys Gly Val Gln Ser Glu Val Lys Leu
             20                  25                  30

Glu Glu Ser Gly Gly Gly Leu Val Gln Pro Gly Gly Ser Met Lys Leu
```

```
                35                  40                  45
Ser Cys Val Ala Ser Gly Phe Thr Phe Ser Gly Tyr Trp Met Ser Trp
    50                  55                  60

Val Arg Gln Ser Pro Glu Lys Gly Leu Glu Trp Val Ala Glu Ile Arg
65                  70                  75                  80

Leu Lys Ser Asp Asn Tyr Ala Thr His Tyr Ala Glu Ser Val Lys Gly
                85                  90                  95

Lys Phe Thr Ile Ser Arg Asp Asp Ser Lys Ser Arg Leu Tyr Leu Gln
                100                 105                 110

Met Asn Ser Leu Arg Ala Glu Asp Ser Gly Val Tyr Tyr Cys Thr Asp
                115                 120                 125

Phe Ile Asp Trp Gly Gln Gly Thr Leu
                130                 135

<210> SEQ ID NO 51
<211> LENGTH: 145
<212> TYPE: PRT
<213> ORGANISM: Mus musculus

<400> SEQUENCE: 51

Ala Leu Gln Leu Leu Ser Thr Gln Asp Leu Thr Met Arg Phe Ser Val
1               5                   10                  15

Gln Phe Leu Gly Val Leu Met Phe Trp Ile Ser Gly Val Ser Gly Asp
                20                  25                  30

Ile Val Ile Thr Gln Asp Glu Leu Ser Asn Pro Val Thr Ser Gly Glu
                35                  40                  45

Ser Val Ser Ile Ser Cys Arg Ser Lys Ser Leu Leu Tyr Lys Asp
    50                  55                  60

Gly Lys Thr Tyr Leu Asn Trp Phe Leu Gln Arg Pro Gly Gln Ser Pro
65                  70                  75                  80

Gln Leu Leu Met Tyr Leu Met Ser Thr Arg Ala Ser Gly Val Ser Asp
                85                  90                  95

Arg Phe Ser Gly Ser Gly Ser Gly Thr Asp Phe Thr Leu Glu Ile Ser
                100                 105                 110

Arg Val Lys Ala Glu Asp Val Gly Val Tyr Tyr Cys Gln Gln Leu Val
                115                 120                 125

Glu Tyr Pro Phe Thr Phe Gly Ser Gly Thr Lys Leu Glu Ile Lys Arg
                130                 135                 140

Thr
145

<210> SEQ ID NO 52
<211> LENGTH: 116
<212> TYPE: PRT
<213> ORGANISM: Artificial Sequence
<220> FEATURE:
<223> OTHER INFORMATION: Description of Artificial Sequence: Humanised
      anti-CD23 antibody VL region

<400> SEQUENCE: 52

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu Tyr Lys
                20                  25                  30

Asp Gly Lys Thr Tyr Leu Asn Trp Tyr Leu Gln Lys Pro Gly Gln Ser
                35                  40                  45

Pro Gln Leu Leu Ile Tyr Leu Met Ser Thr Arg Ala Ser Gly Val Pro
```

```
                50                  55                  60
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Gln Gln Leu
                 85                  90                  95

Val Glu Tyr Pro Phe Thr Phe Gly Gln Gly Thr Lys Val Glu Ile Lys
            100                 105                 110

Arg Thr Val Ala
        115

<210> SEQ ID NO 53
<211> LENGTH: 444
<212> TYPE: PRT
<213> ORGANISM: Artificial Sequence
<220> FEATURE:
<223> OTHER INFORMATION: Description of Artificial Sequence: Humanised
      anti-CD23 antibody VH region

<400> SEQUENCE: 53

Glu Val Gln Leu Val Glu Ser Gly Gly Leu Val Lys Pro Gly Gly
  1               5                  10                  15

Ser Leu Arg Leu Ser Cys Ala Ala Ser Gly Phe Thr Phe Ser Gly Tyr
                 20                  25                  30

Trp Met Ser Trp Val Arg Gln Ala Pro Gly Lys Gly Leu Glu Trp Val
             35                  40                  45

Ala Glu Ile Arg Leu Lys Ser Asp Asn Tyr Ala Thr His Tyr Ala Glu
         50                  55                  60

Ser Val Lys Gly Lys Phe Thr Ile Ser Arg Asp Asp Ser Lys Ser Arg
 65                  70                  75                  80

Leu Tyr Leu Gln Met Asn Ser Leu Lys Thr Glu Asp Thr Ala Val Tyr
                 85                  90                  95

Tyr Cys Thr Asp Phe Ile Asp Trp Gly Gln Gly Thr Leu Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
    210                 215                 220

Pro Cys Pro Ala Pro Glu Leu Ala Gly Ala Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285
```

```
Arg Glu Glu Gln Tyr Asn Ser Thr Tyr Arg Val Val Ser Val Leu Thr
    290                 295                 300
Val Leu His Gln Asp Trp Leu Asn Gly Lys Glu Tyr Lys Cys Lys Val
305                 310                 315                 320
Ser Asn Lys Ala Leu Pro Ala Pro Ile Glu Lys Thr Ile Ser Lys Ala
                325                 330                 335
Lys Gly Gln Pro Arg Glu Pro Gln Val Tyr Thr Leu Pro Pro Ser Arg
                340                 345                 350
Asp Glu Leu Thr Lys Asn Gln Val Ser Leu Thr Cys Leu Val Lys Gly
            355                 360                 365
Phe Tyr Pro Ser Asp Ile Ala Val Glu Trp Glu Ser Asn Gly Gln Pro
    370                 375                 380
Glu Asn Asn Tyr Lys Thr Thr Pro Pro Val Leu Asp Ser Asp Gly Ser
385                 390                 395                 400
Phe Phe Leu Tyr Ser Lys Leu Thr Val Asp Lys Ser Arg Trp Gln Gln
                405                 410                 415
Gly Asn Val Phe Ser Cys Ser Val Met His Glu Ala Leu His Asn His
                420                 425                 430
Tyr Thr Gln Lys Ser Leu Ser Leu Ser Pro Gly Lys
            435                 440

<210> SEQ ID NO 54
<211> LENGTH: 8
<212> TYPE: PRT
<213> ORGANISM: Homo sapiens

<400> SEQUENCE: 54

His Ser Ile Gly Lys Val Ile Ile
1               5
```